(12) United States Patent
Tam

(10) Patent No.: US 6,352,973 B1
(45) Date of Patent: *Mar. 5, 2002

(54) BONE STIMULATING FACTOR

(75) Inventor: Cherk Shing Tam, Oakville (CA)

(73) Assignee: Osteopharm Inc., Oakville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 08/986,627

(22) Filed: Dec. 8, 1997

Related U.S. Application Data

(63) Continuation of application No. PCT/CA96/00401, filed on Jul. 6, 1996, and a continuation-in-part of application No. 08/763,458, filed on Dec. 11, 1996, now Pat. No. 6,117,839, which is a continuation-in-part of application No. 08/487,074, filed on Jun. 7, 1995, now Pat. No. 5,880,094.

(51) Int. Cl.[7] ................ A61K 38/16; C07K 14/435; C12N 15/63; C12N 15/12

(52) U.S. Cl. .................. 514/12; 514/2; 514/13; 514/14; 514/15; 514/16; 530/300; 530/350; 536/23.1; 435/69.1; 435/320.1

(58) Field of Search ................. 530/300, 350, 530/324, 325, 326, 327, 328; 514/2, 12, 13, 14, 15, 16; 536/23.1; 435/69.1, 320.1

(56) References Cited

U.S. PATENT DOCUMENTS

| | | | |
|---|---|---|---|
| 4,877,864 A | 10/1989 | Wang et al. | 530/324 |
| 5,354,557 A * | 10/1994 | Oppermann et al. | 424/423 |
| 5,461,034 A | 10/1995 | Rodan et al. | 514/14 |

FOREIGN PATENT DOCUMENTS

| | | |
|---|---|---|
| EP | 0 499 242 | 8/1992 |
| EP | 0 504 938 | 9/1992 |
| EP | 0 451 867 | 3/1996 |
| WO | 92/10515 | 6/1992 |
| WO | 92/14481 | 9/1992 |
| WO | 92/15615 | 9/1992 |
| WO | 94/20615 | 9/1994 |

OTHER PUBLICATIONS

George et al., Macromolecular Sequencing and Synthesis: Selected Methods and Applications, Schlesinger, ed., Alan R. Liss Inc., New York, pp. 127–149, 1988.*

Bowie et al., Science 247:1306–1310, 1990.*

Wells, Biochemistry 29:8509–8517, 1990.*

Ngo et al., The Protein Folding Problem and Tertiary Structure Prediction, Merz et al., eds., Birkhauser, Boston, pp. 492–495, 1994.*

Schulz et al., Principles of Protein Structure, Springer–Verlag, New York, pp. 14–16, 1979.*

* cited by examiner

*Primary Examiner*—Elizabeth Kemmerer
(74) *Attorney, Agent, or Firm*—Foley & Lardner

(57) ABSTRACT

Polypeptides which stimulate bone growth, associated nucleotide sequences, methods of preparation and use, antibodies and kits are disclosed.

15 Claims, 9 Drawing Sheets

FIG. 13

Active Sequences:

```
SEQ ID NO:1   G I G K R T N E H T A D C K I K P N T L H K K A A E I L M V L D Q N Q P
              1     5         10        15        20        25        30        35

SEQ ID NO:3   G I G K R T N E H T A D A K I K P N T L H K K A A E T L M V L D Q N Q P

SEQ ID NO:4   G I G K R T N E H T A D C K I K P N T L H K K A A E T L M V

SEQ ID NO:5   G I G K R T N E H T A D C K I K P N T L H K K A A

SEQ ID NO:6   G I G K R T N E H T A D C K I K P N T L

SEQ ID NO:7   G I G K R T N E H T A D C K I

SEQ ID NO:8   G I G K R T N E H T A D C K

SEQ ID NO:9           R T N E H T A D C K
```
---
```
SEQ ID NO:10                                  L H K K A A E T L M V L D Q N Q

SEQ ID NO:11                                  L H K K A A E T L M V L D Q N

SEQ ID NO:12                                  L H K K A A E T L M V L D Q

SEQ ID NO:13                                  L H K K A A E T L M V L D

SEQ ID NO:14                      T A D C K I K P N T L H K K A A E T L M V L D

SEQ ID NO:15              R T N E H T A D C K I K P N T L H K K A A E T L M V L D Q N

SEQ ID NO:16              R T N E H T A D C K I
```

BONE STIMULATING FACTOR

This application is a continuation of PCT/CA96/00401 filed Jun. 6, 1996 and a continuation-in-part of U.S. application Ser. No. 08/763,458, filed Dec. 11, 1996, now U.S. Pat. No. 6,117,839, which was a continuation-in-part of U.S. application Ser. No. 08/487,074, filed Jun. 7, 1995, now U.S. Pat. No. 5,880,094.

The present invention relates to polypeptides which stimulate bone growth.

Understanding of issues related to bone growth and strength has progressed over the years, a summary being provided in international patent application No. PCT/CA 94/00144, published under international publication No. WO 94/20615 on Sep. 15, 1994.

Various approaches to treatment of diseases involving reduction of bone mass and accompanying disorders are exemplified in the patent literature. For example, U.S. Pat. No. 4,877,884, issued Oct. 31, 1989 describes human and bovine "bone inductive factors." International patent application published Sep. 17, 1992 under No. 92/15615 describes a protein derived from a porcine pancreas which acts to depress serum calcium levels for treatment of bone disorders that cause elevation of serum calcium levels. European Patent Application No. 504 938 published Sep. 23, 1992 describes the use of di- or tripeptides which inhibit cysteine protease in the treatment of bone diseases. International patent application published Sep. 3, 1992 under No. 92/14481 discloses a composition for inducing bone growth, the composition containing activin and bone morphogenic protein. European Patent Application No. 499 242 published Aug. 19, 1992 describes the use of cell growth factor compositions thought to be useful in bone diseases involving bone mass reduction because they cause osteoblast proliferation. International patent application published Jun. 25, 1992 under No. 92/10515 1992 describes a drug containing the human N-terminal parathyroid hormone (PTH) fragment 1–37. European Patent Application No. 451 867 published Sep. 16, 1991 describes parathyroid hormone peptide antagonists for treating dysbolism associated with calcium or phosphoric acid, such as osteoporosis. U.S. Pat. No. 5,461,034 issued Oct. 24, 1995 to Yissum Research Development Company of the Hebrew University of Jerusalem describes osteogenic growth polypeptides identified from regenerating bone marrow.

A relatively short half life of PTH in the blood serum and the positive effect of intermittent PTH injection on bone volume led the present investigator to the hypothesis that PTH may in some way lead to induction of a second factor into the circulatory system. The presence of such a second factor in blood serum of rats and of humans has thus been investigated.

It has been found possible to isolate from rat blood serum a polypeptide substance which, upon administration to rats incapable of producing PTH (parathyroidectomized rats), produces an increase in the observed bone mineral apposition rate. A nucleic acid probe, based on the amino acid sequence of the rat peptide was synthesized and used to screen a human liver cDNA fetal library in order to isolate human nucleic acid sequence coding for a human bone apposition polypeptide. A polypeptide derived from the nucleic acid sequence was thus chemically synthesized according to the derived sequence Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO:1). It has been observed that the bone apposition rate in intact rats increases in a dose dependent fashion upon administration of this chemically synthesized compound. Reduced bone growth normally observed for ovariectomized rats, was observed not to occur in rats after being administered with the polypeptide over a four week period beginning two weeks after ovariectomization. Bone calcium density was found to be maintained in ovariectomized rats administered with the polypeptide over an eight week period beginning eight weeks after ovariectomization.

It is thought possible that the active polypeptide is a dimer of the foregoing sequence, there being evidence of significant dimer formation, presumably due to a disulfide bridge between two polypeptides having the sequence shown.

A modified form of the polypeptide containing a cys-ala substitution was thus synthesized: Gly Ile Gly Lys Arg Thr Asn Glu His Thr Ala Asp Ala Lys Ile Lys Pro Asn Thr Leu His Lys Lys Ala Ala Glu Thr Leu Met Val Leu Asp Gln Asn Gln Pro (SEQ ID NO:3). Some of the bone stimulatory effects of the "normal" polypeptide (SEQ ID NO:1) were found for the modified polypeptide.

In other experiments, the bone mineral apposition rate in rats administered with rabbit antibodies to the normal polypeptide (SEQ ID NO:1) was found to be suppressed. The suppression was found to be attenuated in rats administered with both the normal polypeptide and antibodies to same.

Further, certain polypeptide fragments of the normal polypeptide (SEQ ID NO:1) have been synthesized and each has been found to have bone stimulatory effects:

SEQ ID NO:4:
  Gly Ile Gly Lys Arg Thr Asn Glu His Thr Ala Asp Cys Lys Ile Lys Pro Asn Thr Leu His Lys Lys Ala Ala Glu Thr Leu Met Val

SEQ ID NO:5:
  Gly Ile Gly Lys Arg Thr Asn Glu His Thr Ala Asp Cys Lys Ile Lys Pro Asn Thr Leu His Lys Lys Ala Ala

SEQ ID NO:6:
  Gly Ile Gly Lys Arg Thr Asn Glu His Thr Ala Asp Cys Lys Ile Lys Pro Asn Thr Leu

SEQ ID NO:7:
  Gly Ile Gly Lys Arg Thr Asn Glu His Thr Ala Asp Cys Lys Ile

SEQ ID NO:8:
  Gly Ile Gly Lys Arg Thr Asn Glu His Thr Ala Asp Cys Lys

SEQ ID NO:9:
  Arg Thr Asn Glu His Thr Ala Asp Cys Lys

Further, the polypeptide identified as SEQ ID NO:7 has been found to increase bone calcium content of ovariectomized rats when administered over a period of eight or twelve weeks.

Other polypeptide fragments of the normal polypeptide (SEQ ID NO:1) have also been synthesized and have been found to lack the bone stimulatory effect found for the normal polypeptide.

SEQ ID NO:10:
  Leu His Lys Lys Ala Ala Glu Thr Leu Met Val Leu Asp Gln Asn Gln

SEQ ID NO:11:
  Leu His Lys Lys Ala Ala Glu Thr Leu Met Val Leu Asp Gln Asn

SEQ ID NO:12:
  Leu His Lys Lys Ala Ala Glu Thr Leu Met Val Leu Asp Gln

SEQ ID NO:13:
  Leu His Lys Lys Ala Ala Glu Thr Leu Met Val Leu Asp

SEQ ID NO:14:
  Thr Ala Asp Cys Lys Ile Lys Pro Asn Thr Leu His Lys Lys Ala Ala Glu Thr Leu Met Val Leu Asp

SEQ ID NO:15:
Arg Thr Asn Glu His Thr Ala Asp Cys Lys Ile Lys Pro Asn Thr Leu His Lys Lys Ala Ala Glu Thr Leu Met Val Leu Asp Gln Asn

SEQ ID NO:16:
Arg Thr Asn Glu His Thr Ala Asp Cys Lys Ile

The present invention thus includes a polypeptide having an amino acid sequence corresponding to SEQ ID NO:1 with (a) from one to about four 4 amino acids deleted from the N-terminus of SEQ ID NO:1 (b) one to about 22 amino acids deleted from the C-terminus of SEQ ID NO:1, or both (a) and (b): or a functionally equivalent homologue. Correspondingly, the invention includes a polypeptide having an amino acid sequence corresponding to SEQ ID NO:3 with (a) from one to about four 4 amino acids deleted from the N-terminus of SEQ ID NO:3 (b) one to about 22 amino acids deleted from the C-terminus of SEQ ID NO:3, or both (a) and (b); or a functionally equivalent homologue. Sequence homology in polypeptides and proteins is understood to those skilled in the art, as discussed, for example in Molecular Cell Biology (H. Lodish, D. Baltimore, A. Berk, S. L. Zipursky, P. Matsudaira and J. Darnell, Scientific American Books, New York City, Third Edition, 1995). Likewise, the invention includes a polypeptide having an amino acid sequence corresponding to SEQ ID NO:4 with (a) up to about four 4 amino acids deleted from the N-terminus of SEQ ID NO:4, (b) up to about 16 amino acids deleted from the C-terminus of SEQ ID NO:4, or both (a) and (b); or a functionally equivalent homologue. The invention includes a polypeptide having an amino acid sequence corresponding to SEQ ID NO:5 with (a) up to about four 4 amino acids deleted from the N-terminus of SEQ ID NO:5, (b) up to about 11 amino acids deleted from the C-terminus of SEQ ID NO:5, or both (a) and (b); or a functionally equivalent homologue. The invention includes a polypeptide having an amino acid sequence corresponding to SEQ ID NO:6 with (a) up to about four 4 amino acids deleted from the N-terminus of SEQ ID NO:6, (b) up to about 5 amino acids deleted from the C-terminus of SEQ ID NO:6, or both (a) and (b); or a functionally equivalent homologue. The invention includes a polypeptide having an amino acid sequence corresponding to SEQ ID NO:7 with (a) up to about four 4 amino acids deleted from the N-terminus of SEQ ID NO:7, (b) up to about 1 amino acids deleted from the C-terminus of SEQ ID NO:4, or both (a) and (b); or a functionally equivalent homologue. The invention also includes a polypeptide having an amino acid sequence corresponding to SEQ ID NO:8 with up to about four 4 amino acids deleted from the N-terminus or a functionally equivalent homologue. The invention includes a polypeptide having an amino acid sequence corresponding to SEQ ID NO:9 or a functionally equivalent homologue thereof.

The inventive polypeptide can be synthetic and the amino acid sequence can have a molecular weight in the range of from about 1000 to 4000.

The invention includes a polypeptide having a sequence of amino acids sufficiently duplicative of another, i.e., second polypeptide having an amino acid sequence corresponding to SEQ ID NO:1 (or SEQ ID NO:3) with (a) from one to about four 4 amino acids deleted from the N-terminus of SEQ ID NO:1 (or SEQ ID NO:3) (b) one about 22 amino acids deleted from the C-terminus of SEQ ID NO:1 or SEQ ID NO:3, or both (a) and (b), or a functionally equivalent homologue thereof, such that the polypeptide is encoded by a DNA that hybridizes under stringent conditions with DNA encoding the second polypeptide.

In another aspect the invention is a synthetic polypeptide having in vivo bone stimulatory activity in mammals and which increases mineral content (i.e., calcium) in bones of mammals, having an amino acid sequence which is at least about 19% conserved in relation to the amino acid sequence identified as SEQ ID NO:1 and having at least one amino acid deleted therefrom, or a functionally equivalent homologue.

The invention includes a synthetic polypeptide having in vivo bone stimulatory activity in mammals and which increases mineral content in bones of mammals, having an amino acid sequence which is at least about 22% conserved in relation to the amino acid sequence identified as SEQ ID NO:1 and having at least one amino acid deleted therefrom.

The invention includes a synthetic polypeptide having in vivo bone stimulatory activity in mammals and which increases mineral content in bones of mammals, having an amino acid sequence which is at least about 25% conserved in relation to the amino acid sequence identified as SEQ ID NO:1 and having at least one amino acid deleted therefrom.

The invention includes a synthetic polypeptide having in vivo bone stimulatory activity in mammals and which increases mineral content in bones of mammals, having an amino acid sequence which is at least about 28% conserved in relation to the amino acid sequence identified as SEQ ID NO:1 and having at least one amino acid deleted therefrom.

The invention includes any of the foregoing synthetic polypeptides in which at least six amino acids deleted from the polypeptide sequence; or in which at least eleven amino acids deleted from the sequence; or in which at least sixteen amino acids deleted from the sequence; or in which at least twenty-one amino acids deleted from the sequence; or in which at least twenty-six amino acids deleted from the sequence.

The invention includes a polypeptide having a sequence of amino acids sufficiently duplicative of one of the foregoing synthetic polypeptides such that the polypeptide is encoded by a DNA that hybridizes under stringent conditions with DNA encoding the synthetic polypeptide.

In another aspect the invention is a polypeptide exhibiting bone stimulatory activity in mammals, the polypeptide having the sequence identified as SEQ ID NO:1, SEQ ID NO:3, SEQ ID NO:4, SEQ ID NO:5, SEQ ID NO:4, SEQ ID NO:6, SEQ ID NO:7, SEQ ID NO:8, or SEQ ID NO:9; analogues thereof wherein the amino acids in the sequence may be substituted, deleted or added, so long as the bone stimulatory activity in mammals derived the three dimensional structure of the sequence is preserved; and conjugates of each of the polypeptides or analogues thereof, wherein if the polypeptide sequence has that identified as SEQ ID NO:1, then there is at least one amino acid deleted therefrom. The invention includes a polypeptide that has a sequence of amino acids sufficiently duplicative of such a bone stimulatory polypeptide (or a functionally equivalent homologue thereof) that the polypeptide is encoded by a DNA that hybridizes under stringent conditions with DNA encoding the bone stimulatory polypeptide.

In another aspect, the invention is a polypeptide that includes an amino acid sequence that is between 19% and 90% conserved in relation to the amino acid sequence identified as SEQ ID NO:1; or an amino acid sequence that is between 19% and 86% conserved in relation to the amino acid sequence identified as SEQ ID NO:1; or an amino acid sequence that is between 19% and 42% conserved in relation to the amino acid sequence identified as SEQ ID NO:1; or an amino acid sequence that is between 19% and 56% conserved in relation to the amino acid sequence identified as SEQ ID NO:1; or an amino acid sequence that is between 19% and 42% conserved in relation to the amino acid sequence identified as SEQ ID NO:1; or an amino acid sequence that is between 19% and 39% conserved in relation to the amino acid sequence identified as SEQ ID NO:1: or an amino acid sequence that is between 19% and 28% conserved in relation to the amino acid sequence identified as SEQ ID NO:1; or an amino acid sequence that is between 28% and 90% conserved in relation to the amino acid sequence identified as SEQ ID NO:1; or an amino acid sequence that is between 28% and 86% conserved in relation to the amino acid sequence identified as SEQ ID NO:1; or an amino acid sequence that is between 28% and 69% conserved in relation to the amino acid sequence identified as SEQ ID NO:1; or an amino acid sequence that is between 28% and 56% conserved in relation to the amino acid sequence identified as SEQ ID NO:1; or an amino acid sequence that is between 28% and 42% conserved in relation to the amino acid sequence identified as SEQ ID NO:1: or an amino acid sequence that is between 28% and 39% conserved in relation to the amino acid sequence identified as SEQ ID NO:1; or a functionally equivalent homologue that has bone stimulatory activity in a mammal.

The polypeptide can be a chimeric bone stimulating factor that includes any of the amino acid sequences described above as part of the invention.

The invention includes an agent for use in prevention and treatment of a bone reduction related disease that includes any polypeptide described above as part of the invention, including of course a chimeric polypeptide, as an active ingredient.

The invention is thus also a pharmaceutical composition for promoting bone growth, having a therapeutically effective amount of any polypeptide described above as part of the invention.

The invention includes a method of increasing bone growth in a mammal by administering a therapeutically effective amount of a polypeptide (or a pharmaceutical composition including the polypeptide) described above as part of the invention.

The invention includes the treatment of osteoporosis, promotion of bone growth in a mammal or treatment of a human or a bone reduction related disease.

The invention includes the use of a polypeptide having a sequence according to any polypeptide of the invention in the preparation of a medicament for use in promoting bone growth of the treatment of osteoporosis, etc.

The invention includes a diagnostic kit for determining the presence of a polypeptide of the invention, in which the kit includes an antibody to a polypeptide (or polypeptides) linked to a reporter system wherein the reporter system produces a detectable response when a predetermined amount of the polypeptide (or polypeptides) and the antibody become bound together.

The invention includes an antibody which binds to a polypeptide of the invention. Particularly, the invention includes an antibody which binds to such a polypeptide when the antibody is synthesized using the polypeptide.

The invention includes molecules, such as isolated nucleotide sequences related to polypeptides of the invention. For example, the invention includes an isolated DNA fragment which encodes the expression of any of the polypeptides of the invention. It is of course understood that such fragments can vary from one another due to the degeneracy of the genetic code. Further, the invention includes a vector that has incorporated into it any such DNA sequence.

The invention includes an isolated DNA sequence encoding any amino acid sequence of the invention, or an analogue thereof, wherein the amino acids in the sequence may be substituted, deleted or added, so long as bone stimulatory activity in mammals derived from the three dimensional conformation of the sequence is preserved in a polypeptide having the amino acid sequence; sequences which hybridize to the DNA and encode an amino acid sequence of a polypeptide which displays bone stimulatory activity in mammals; and and DNA which differs from the sequence due to the degeneracy of the genetic code.

The invention thus includes processes of producing any polypeptide of the invention, including a process which includes: a) preparing a DNA fragment containing a nucleotide sequence that encodes such a polypeptide; b) incorporating the DNA fragment into an expression vector to obtain a recombinant DNA fragment which contains the DNA fragment and is capable of undergoing replication; c) transforming a host cell with the recombinant DNA fragment to isolate a transformant which can express the polypeptide; and d) culturing the transformant to allow the transformant to produce the polypeptide and recovering the polypeptide from resulting cultured mixture.

BRIEF DESCRIPTION OF THE DRAWINGS

In the following description, reference is made to accompanying drawings, wherein, FIG. 1 graphically depicts the bone mineral apposition rate ($\mu$m per day) in rats provided with the chemically synthesized human N-acetyl (N-terminus) polypeptide (SEQ ID NO:2) through implantation in parathyroidectomized rats. The error bars indicate ±1 standard deviation (S.D.). The value of p was less than 0.001.

FIG. 13 illustrates the amino sequences of the various polypeptides tested, active polypeptides being shown above the mid-line and sequences which were not found to stimulate bone growth being below the mid-line.

INDUCTION OF HYPERPARATHYROID STATE IN RATS

Figure 1:
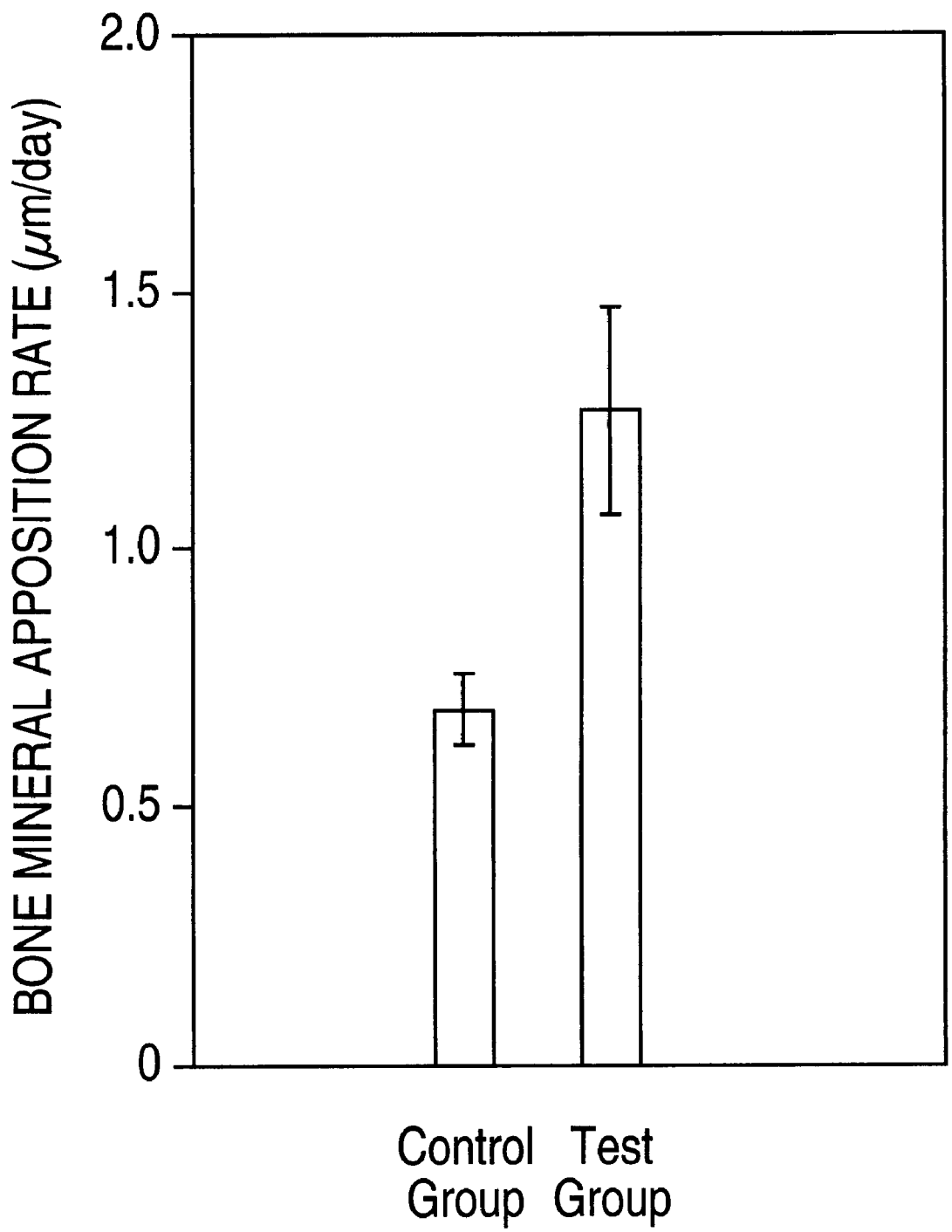

Calcium deficient diet (Catalogue #113034, Lot #0186-3) used to induce the hyperparathyroid state was purchased from Dyets, 2508 Easton Avenue, Bethlehem, Pa. 18017, U.S.A. This diet contains 0.1% calcium and 0.05% phosphorus. The calcium sufficient diet (Catalogue #113035, Lot #01864) used for control animals contains 0.5% calcium and 0.055% phosphorus as specified by the manufacturer, Dyets. Both diets contains vitamin D at a concentration of 1 i.u./g. The diets are pelleted in pallets and each animal was provided with 10 pellets a day along with demineralized water. Test animals were put on those diets for a period of two weeks.

EXPERIMENTAL RATS

The Sprague-Dawley rat from Charles River laboratory was the standard test animal. Male rates weighting between 200 to 250 g at the time of purchase were used, the rats being housed in pairs in identical cages.

TETRACYCLINE LABELING OF BONE FOR DETERMINATION OF BONE MINERAL APPOSITION RATE IN RATS (26)

It has been demonstrated that a dose of tetracycline 24 mg/kg of body weight when injected intravenously into a rate is cleared from the circulation within half an hour. That is, by such time the serum tetracycline level is not measurable by bioassay. It has also been shown that intermittent labeling doses of from 6 to 24 mg/kg b.w., result in the same measured rate of bone apposition. Thus, tetracycline given intermittently, that is, as pulse labels in this dose range appears to be a satisfactory way of labeling bone for the study of the mineral apposition rate.

It has also been shown, however, that in a bone forming location, the BMU, the deposition of mineralized bone matrix can be subject to interruption. Such interruption is most likely to occur when the interval between two doses of tetracycline is longer than 7 days. Such interruption is possible due to there being more than one group of osteoblasts activated in succession over the same matrix surface location. Such osteoblast activation may be random or non-random. To avoid the influence of this phenomenon on the measurement of the rate of bone mineral deposition, 48 hour intervals between labels were used. Tetracycline hydrochloride, which has a serum half life of 8 hours when a therapeutic dose is used, was used exclusively.

Tetracycline is excited by long UV light (i.e., with a range close to the blue range) and a bright yellow fluorescence is emitted, which fluorescence is detectable in bone sections viewed with a fluorescence microscope. Tetracycline labels a bone surface when a newly formed collagen matrix begins to incorporate calcium and when such surface is sectioned, the tetracycline appears as a yellow fluorescent band. A subsequently administered dose of tetracycline appears as a second band located superficial to the first band. The distance between the two bands represent the thickness of bone matrix formed in the interval between the two doses. The rate of deposition can be calculated by dividing the distance with the time interval between doses. Errors can be introduced by cuts which are not perpendicular to the growing bone surface. To reduce this error, only sites in which the two bands were distinct and parallel to each other were used. Measurements made on 10 randomly chosen sites fulfilling this requirement were chosen to give readings close to the arithmetic mean of the rate.

Figure 2:
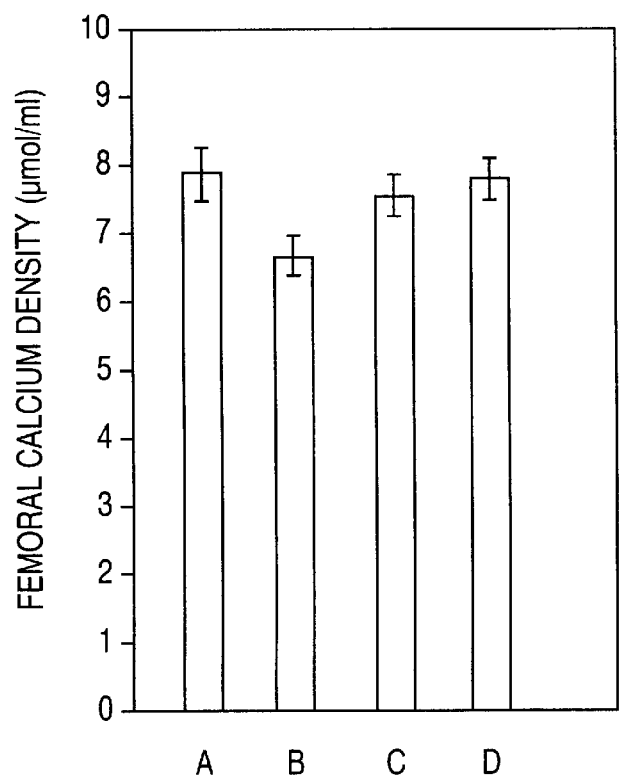
FIG. 2 graphically depicts right femoral bone calcium density of rats treated over a four week period. Group A rats were ovariectomized and injected daily with the chemically synthesized normal peptide (SEQ ID NO:1). Group B rats were ovariectomized and injected daily with control solution. Group C rats were subject to sham ovariectomization operations and injected daily with control solution. Group D were intact rats injected daily with control solution. The error bars indicate ±1 standard deviation (S.D.).

The measuring system used was Leitz scanning light microscope photometer MPV-CD with a UV source being provided by a 100 W stabilized mercury burner. Sections were generally magnified using 16× objective using a moving scanning slit, the intensity of the fluorescent band was amplified and recorded. This light signal was transformed into digital output and the profile of the tetracycline intensity recorded. The distance between the intensity peaks was taken as the distance between two tetracycline bands, as shown in FIG. 1. The instrument carries a mechanical error of less than 5%. The distance measured was periodically calibrated with a microscopic grid and a good correlation was found, as shown in FIG. 2.

SKELETAL SITE FOR THE STUDY OF THE BONE MINERAL APPOSITION RATE IN RATS

The lower metaphysis of the right femur was generally chosen as the site of measurement, unless otherwise indicated. The site is located about 1 mm above the lower femoral growth plate and extends upwards towards the shaft for a distance of about 5 mm.

HISTOLOGICAL PREPARATION OF RAT BONE MATERIAL

The bone sample was dissected out of the animal after sacrifice. The bone sample was immediately fixed in a 10% aqueous solution of formaldehyde buffered to pH 7.2 to 50 mM phosphate buffer. A low pH will cause tetracycline to leach out from the bone matrix. After a 24 hour fixation period the sample was processed as follows.

| | |
|---|---|
| 80% ethanol | 24 hours |
| 95% ethanol | 24 hours |
| Absolute ethanol | 24 hours |
| Absolute ethanol | 24 hours |
| acetone | 24 hours |
| Spurr's medium:acetone 1:1 | 24 hours |

| Spurr's medium:acetone 1:4 | 24 hours |
| Spurr's medium | 24 hours |

The sample was then embedded in a fresh change of Spurr's medium and cured at 45° C. for 24 hours; and then cured at 80° C. for another 24 hours.

The cured block was cut into 400 μm thick sections using a Leitz saw microtoms equipped with a diamond charged blade. The relatively thick sections were ground down between two ground glass plates pre-roughened with carborundum powder to a final thickness of about 10 μm. Water being used as the grinding lubricant. The thin sections were dried and mounted unstained in Permount (Fisher).

PARATHYROIDECTOMIZATION OF RATS FOR ASSAYING THE EFFECT OF TEST MATERIALS ON BONE APPOSITION

Male Spraque-Dawley rats of between about 200 to 250 g. were parathyroidectomized under general nembutal anesthesia. The parathyroid glands were destroyed by repeated freezing and thawing. One week after the surgery, the animals were anesthetized again and 0.5 ml of blood taken from the tail vein. The animal was then deprived of food overnight. The next morning, the animal was again anaesthetized and 0.5 ml of blood taken from the tail vein. The serum calcium before and after fasting was measured. A fall of the serum calcium in the fasting state to 1.8 mM or lower was taken as an indication of successful surgery. The test material as then injected into the tail vein followed by the first dose of tetracycline or injected intramuscularly. The second tetracycline label was given 48 hours later and the animal killed 24 hours thereafter by carbon dioxide narcosis. The bone sample was then taken for bone mineral apposition rate measurement.

The applicable methodology as described in the General Methodology section of international patient application No. PCT/CA94/00144 was followed here.

TOXICITY EXPERIMENTS INVOLVING N-TERMINAL ACETYL CHEMICALLY SYNTHESIZED POLYPEPTIDE (SEQ ID NO:2)

A miniosmotic pump (Alzet) was loaded with about 1.5 ml of the chemically synthesized peptide having an N-terminal acetyl group (SEQ ID NO:2) in 0.1% acetic acid so as to give a calculated daily delivery of about 25 μg per day. A pump was implanted under the subcutaneous fascia of the dorsal aspect of the left side of the thorax of five rats which had been parathyroidectomized seven days earlier. Five similarly parathyroidectomized rats received similar implants containing only 0.1% acetic acid. Five intact rats were also used as controls.

Twenty-eight days later 0.5 ml of an aqueous solution of tetracycline hydrochloride was injected intramuscularly into the right gluteus maximus of each of the implanted rats, as described previously. Another 48 hours later, a second injection of tetracycline hydrochloride solution was injected. The rats were sacrificed another 24 hours later.

The bone mineral apposition rate was determined by examination of a cross-section of the lower metaphysis of the right femur of each of the ten rats which had been given implants. The results are summarized in Table One depicted graphically in FIG. 1

TABLE ONE

Comparison of the Group Arithmetic Means Among Groups

|  | Test Group | Control Group |
| --- | --- | --- |
| Mean | 1.27 μm/d | 0.67 μm/d |
| S.D. | 0.18 μm/d | 0.08 μm/d |
| N | 5 | 5 |
|  | t | d.f |
| Test Group vs Control Group | 7.14 | 8 |

Histological evaluation of selected tissues of the five rats of each of the groups indicated in Table One were carried out microscopically. No evidence of toxic lesions was found.

EXPERIMENTS INVOLVING OVARIECTOMIZED RATS AND THE NORMAL CHEMICALLY SYNTHESIZED POLYPEPTIDE (SEQ ID NO:1), ADMINISTRATION OVER A FOUR WEEK PERIOD

Ovariectomies were performed on six female Sprague-Dawley rats, each sedated with 1 mg of sodium barbiturate I.P. Sham operations were carried out a second group of six rats. The rats were given two weeks to recover from the operations.

The six ovariectomized rats were injected subcutaneously with 100 μl of a 0.1% acetic acid solution containing 100 μg of the chemically synthesized peptide (SEQ ID NO:1) every 24 hours for 28 days. On day 25, a tetracycline hydrochloride solution was injected intramuscularly into each rat so as to give 24 mg per Kg of body weight, as described previously. One day 27, a second dose of tetracycline hydrochloride was injected and the rats were sacrificed on the 28th day.

A second group of six ovariectomized rats, was similarly treated with a 0.1% acetic acid solution containing no peptide over the same 28 day period. A third group of six rats, each of which had undergone the sham operation, was similarly treated with a 0.1% acetic acid solution containing no peptide over the same 28 day period. A fourth group of six intact rats was similarly treated with a 0.1% acetic acid solution containing no peptide over the same 28 day period.

Postmortem blood was taken by cardiac puncture and serum frozen until analyzed. A full autopsy was performed on each rat. No ill effects were observed in the rats treated with the polypeptide.

Each of the right femurs was dissected out from its soft tissue, fixed for two days, and X-rays taken at 70 kV for 1 min., 2 min., and 3 min. The 3 minute exposures gave the most satisfactory results. The bone densities of the femurs from the second group of rats, the ovariectomized rats not treated with the peptide, showed a visibly lower bone density.

The right femur of each rat was decalcified separately. The decalcification fluid consisted of 10% formic acid (v/v) and 5% sodium citrate (w/v) at pH 3.0. Each bone was placed in 6 ml of the decalcification fluid. The fluid was replaced after 4 days, again after another 4 days, again after another 2 days, and again after another 3 days. After another 2 days, the decalcification fluid was removed and replaced by deionized water, and the sample agitated for 2 days. The water changed after two days and again after another day. After another day, all of the fluid samples for each rat were combined and the final volume of each adjusted to 50 ml with deionized water.

The volume of each right femur was determined by determining the volume of water displaced when the bone was immersed in water. The calcium concentration of each sample was determined according to standard methods and the calcium density of each bone calculated. The results are tabulated in Table Two and graphically depicted in FIG. 2. As can be seen, the bone calcium concentration measured for the ovariectomized rats treated with the peptide (SEQ ID NO:1) appears to be normal, while the calcium concentration of the untreated ovariectomized rats is depressed.

TABLE TWO

Right Femoral Calcium Concentration of Ovariectomized Rats

|  | Group A | Group B | Group C | Group D |
|---|---|---|---|---|
| Mean ($\mu$mol/ml) | 7.57 | 6.61 | 7.45 | 7.69 |
| N | 6 | 6 | 6 | 6 |
| S.D. | 0.38 | 0.29 | 0.28 | 0.31 |

| GROUP | t | d.f. | p |
|---|---|---|---|
| A vs B | 4.90 | 10 | <0.001 |
| A vs C | 0.62 | 10 | >0.5 |
| A vs D | 0.60 | 10 | >0.5 |
| B vs C | 5.08 | 10 | <0.001 |
| B vs D | 6.20 | 10 | <0.001 |
| C vs D | 1.40 | 10 | >0.1 |

Figure 3:
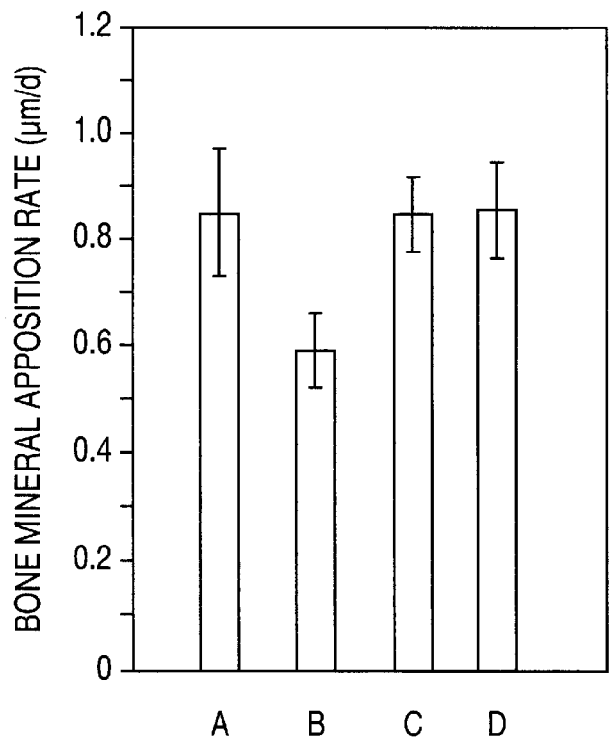
FIG. 3 graphically depicts the bone mineral apposition rate of rats as determined by tetracycline labelling after treatment as described in connection with FIG. 2. The error bars indicate ±1 standard deviation (S.D.).

The bone mineral apposition rate was determined, as described previously, by measurement of the lower metaphysis of the left femur. The results are tabulated in Table Three and graphically depicted in FIG. 3.

TABLE THREE

Bone Mineral Apposition Rates of Ovariectomized Rats

|  | Group A | Group B | Group C | Group D |
|---|---|---|---|---|
| Mean ($\mu$mol/ml) | 0.90 | 0.59 | 0.85 | 0.86 |
| N | 6 | 6 | 6 | 6 |
| S.D. | 0.12 | 0.07 | 0.07 | 0.09 |

| GROUP | t | d.f. | p |
|---|---|---|---|
| A vs B | 5.39 | 10 | <0.001 |
| A vs C | 0.87 | 10 | >0.5 |
| A vs D | 0.21 | 10 | >0.5 |
| B vs C | 6.29 | 10 | <0.001 |
| B vs D | 5.93 | 10 | <0.001 |
| C vs D | 0.21 | 10 | >0.5 |

EXPERIMENTS INVOLVING OVARIECTOMIZED RATS AND THE NORMAL CHEMICALLY SYNTHESIZED POLYPEPTIDE, ADMINISTRATION OVER AN EIGHT WEEK PERIOD

Eight weeks after ovariectomization, five ovariectomized rats were injected subcutaneously with 100 $\mu$l of a 0.1% acetic acid solution containing 100 $\mu$g of the chemically synthesized peptide in which the N-terminal amino group was modified with an acetyl group (SEQ ID NO:2). This was done every 24 hours for eight weeks. On day 54, a tetracycline hydrochloride solution was injected intramuscularly into the right gluteus maximus of each rat so as to give 24 mg per Kg of body weight, as described previously. One day 56, a second dose of tetracycline hydrochloride was injected and the rats were sacrificed on the 57th day.

A second group of seven ovariectomized rats, was similarly treated with a 0.1% acetic acid solution containing no peptide over the same period. A third group of five rats, each of which had undergone the sham operation, was similarly treated with a 0.1% acetic acid solution containing no peptide over the same period. A fourth group of five intact rats was similarly treated with a 0.1% acetic acid solution containing no peptide over the same 8 week period. Two rats of the second group became ill during the 8 week period and were sacrificed prematurely.

Postmortem blood was taken by cardiac puncture and serum frozen until analyzed. An autopsy was performed on each rat. No obvious pathology was observed in the rats except for surgical scars and atrophy of the uterus and vagina of ovariectomized rats.

Figure 4:
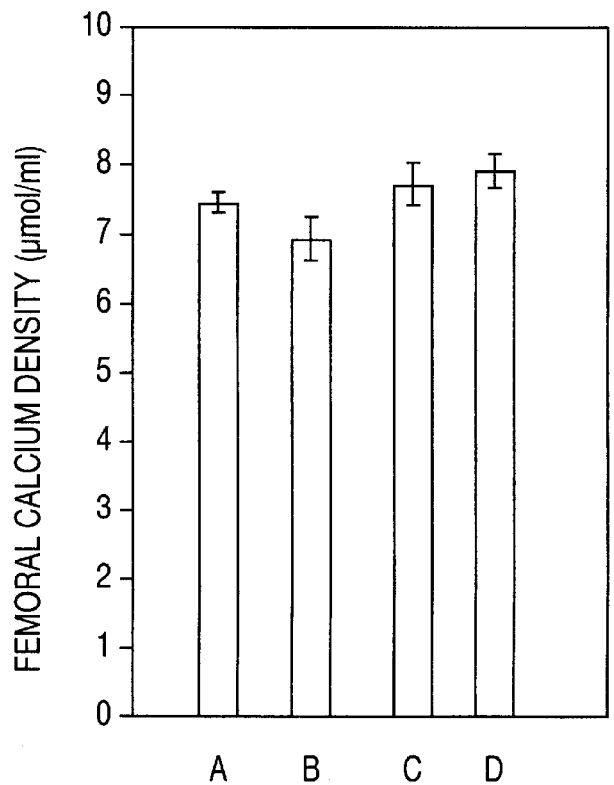
FIG. 4 graphically depicts femoral bone calcium concentration of rats treated over an eight week period. Group A rats were ovariectomized and injected daily with the chemically synthesized normal peptide (SEQ ID NO:1) beginning eight weeks after the operation. Group B rats were similarly ovariectomized and injected daily with control solution. Group C rats were subjected to sham ovariectomization operations and injected daily with control solution. Group D were intact rats injected daily with control solution. The error bars indicate ±1 standard deviation (S.D.).

The right femurs were decalcified and calcium density determined as before. The results were presented in Table Four and FIG. 4.

TABLE FOUR

Right Femoral Calcium Concentration of Ovariectomized Rats

|  | Group A | Group B | Group C | Group D |
|---|---|---|---|---|
| Mean ($\mu$mol/ml) | 7.37 | 6.89 | 7.69 | 7.87 |
| N | 5 | 5 | 5 | 5 |
| S.D. | 0.15 | 0.32 | 0.30 | 0.24 |

| GROUP | t | d.f. | p |
|---|---|---|---|
| A vs B | 3.85 | 6 | <0.005 |
| A vs C | 1.17 | 6 | >0.2 |
| A vs D | 3.01 | 6 | <0.1 |
| B vs C | 4.03 | 6 | <0.005 |
| B vs D | 5.41 | 6 | <0.001 |
| C vs D | 1.60 | 6 | >0.1 |

SYNTHESIS OF ANTIBODIES TO CHEMICALLY SYNTHESIZED PROTEIN (SEQ ID NO:1)

The chemically synthesized protein (SEQ ID NO:1) was coupled to KLH (keyhole limpet hemocyanin) with three different cross-linkers, as described below.

GLUTARALDEHYDE COUPLING

In 2.5 ml of a PBS solution made up of 2.7 mM KCl, 1.2 mM $KH_2PO_4$, 138 mM NaCl, 8.1 mM $Na_2HPO_4$, were diluted 5 mg of the peptide (SEQ ID NO:1) to obtain a final peptide concentration of 2 mg/ml. 10 mg of KLH were diluted in 5.0 ml PBS to obtain a final concentration of 2 mg/ml. To 1.25 ml of the KLH solution were added 1.25 ml of the peptide solution. Glutaraldehyde was added to a final concentration of 0.25%. The resultant solution was stirred for 1 hour at room temperature. After stirring, the solution was dialysed against 1 litre of PBS. The PBS was changed three times.

CARBODIIMIDE (EDC) COUPLING

Peptide and KLH solutions were prepared as described in the preceding section. To 1.25 ml KLH solution were added 1.25 ml peptide solution. To the resultant solution were added 2.5 mg of EDC. The solution was stirred constantly at room temperature for 4 hours and then dialysed against 1 litre of PBS. The PBS was changed three times.

M-MALEIMIDOBENZOYL-N-HYDROXYSUCCINIMIDE ESTER (MBS) COUPLING

To 500 $\mu$l of $H_2O$ were added 5 mg of the peptide and the pH was adjusted to 8.5 with NaOH, to obtain a final concentration of 10 mg/ml. Citraconic anhydride was diluted in $H_2O$ to a concentration of 10 mg/ml. 500 $\mu$l of the anhydride solution were added to the peptide solution 100 $\mu$l at a time with adjustment of the pH to 8.5 between each addition. The solution was then stirred constantly at room temperature for 1 hour. This was followed by the addition of 100 $\mu$l of 1M sodium phosphate buffer (pH 7.2) and then 900 $\mu$l of 100 mM sodium phosphate buffer (pH 7.2). Sulfo-MBS was diluted in $H_2O$ to a concentration of 25 mg/ml and 400 $\mu$l of this solution were added to the peptide solution to obtain an MBS concentration of about 5 mg/ml. This solution as stirred constantly at room temperature for 30 minutes. 6 μl of β-mercaptoethanol were added for a final β-mercaptoethanol concentration of 35 mM. The solution was stirred constantly at room temperature for 1 hour. KLH was dissolved in PBS at 3 mg/ml and 2.5 ml were added to the peptide solution. The solution was stirred constantly at room temperature for 3 hours and then dialysed against 1 litre of PBS, with three changes of the PBS. The final peptide concentration was about 1 mg/ml and the final KLH concentration was about 1.5 mg/ml.

Antibody Generation

Rabbits were injected with the synthetic peptide solutions as follows. 250 μl each of the glutaraldehyde- and EDC-coupled peptide solutions were together mixed with 500 μl of Freund's adjuvant. This solution was injected intramuscularly into the rear legs of a rabbit, 500 μl per leg. The total amount of injected peptide was 0.5 mg. 500 μl of the synthetic peptide coupled to KLH with MBS were mixed with 500 μl of Freund's adjuvant. This solution was injected intramuscularly into the rear legs of another rabbit, 500 μl per leg. The total amount of injected peptide was 0.5 mg.

The synthetic peptide was loaded onto two lanes, 1.5 μg and 4 μg of a gel (18% running, 5% stacking). The gel was blotted overnight at 30 V and blocked with 3% milk in PBS. The gel was incubated overnight with rabbit serum diluted 1:250 in 1% milk/PBS followed by incubation with goat anti-rabbit-alkaline phosphatase diluted 1:100 for 1 hour. The gel was then developed with substrate. The synthetic peptide was seen by comasie blue staining. The peptide was detected by the second bleed of each rabbit and was not detected by the preimmune serum of either rabbit.

Interaction between immobilized peptide and serum antibodies was further studied through surface plasmon resonance using BIAcore™. The synthetic peptide was covalently immobilized on a dextran matrix by amine coupling. Rabbit serum of different dilutions were injected over the surface for five minutes and the amount of antibody bound to the immobilized peptide determined. The titer is defined as the last dilution of the serum giving a positive response, that is, greater than 50 Resonance Units. Using this approach, antibodies were found to be present in serum from both rabbits and the interaction can be blocked by preincubating the serum with the peptide. Antibodies in serum of the rabbits were found not to interact with an immobilized unrelated peptide.

Experiments Involving Rats and Antibodies to the Chemically Synthesized Peptide

Antibody serum was prepared in 10 mM Tris.Cl at pH 7.4. Each of five rats received 100 μl of the solution by injection into the left gluteus maximus. Each rat of a second group of five rats was treated similarly, but with an additional injection of solution containing 45 μg of the polypeptide (SEQ ID NO:1) into the right gluteus maximus. Each rat of a third group of five rats received an injection of 100 μl of 10 mM Tris.Cl at ph 7.0.

Each of the fifteen rats was then injected as before with tetracycline hydrochloride, in the amount of 24 mg per Kg of body weight. A second dose of tetracycline hydrochloride was injected about 48 hours later. The rats were sacrificed after about another 24 hours.

Figure 5:
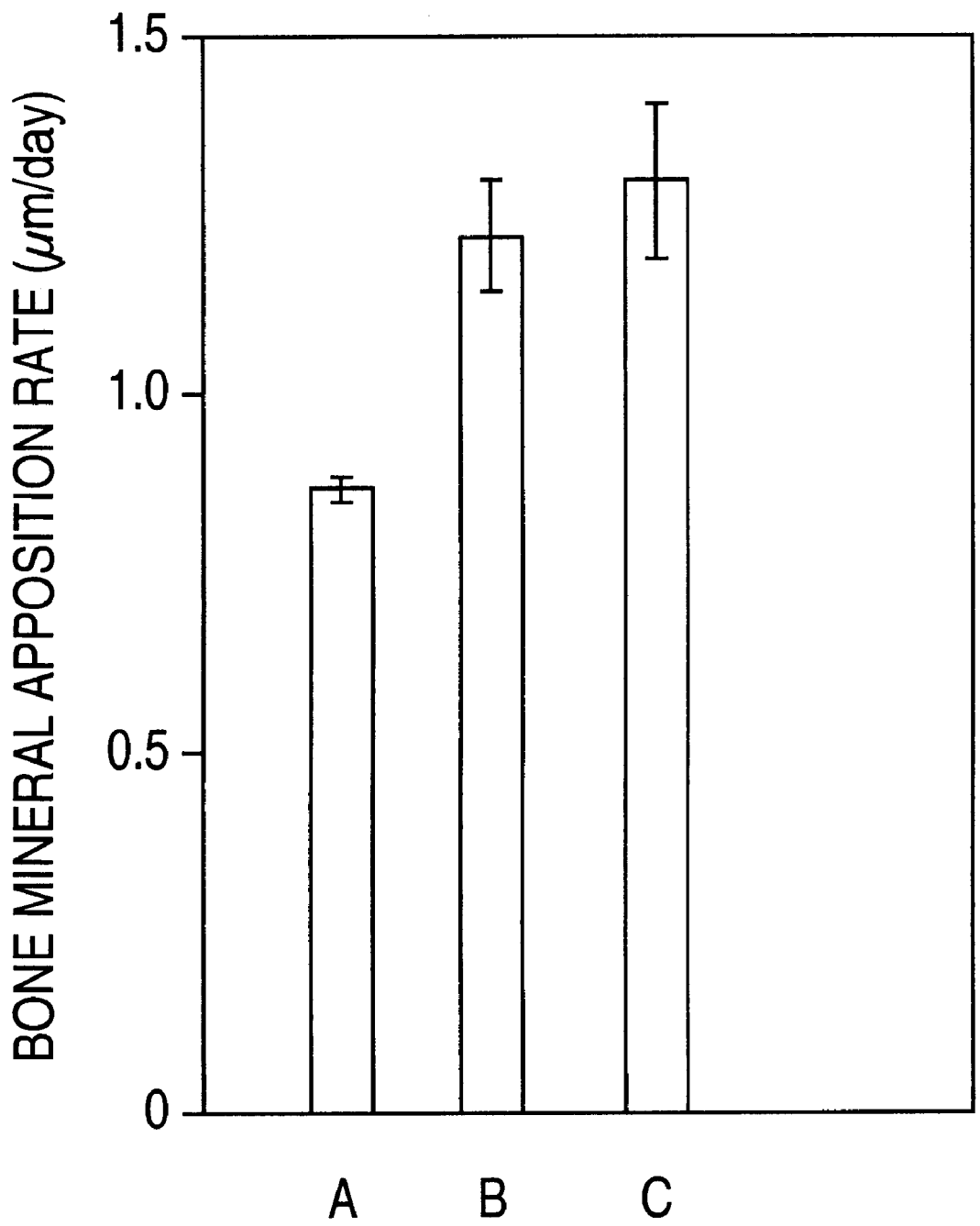
FIG. 5 graphically depicts the bone mineral apposition rate of intact rats as determined by tetracycline labeling. Group A rats were treated with rabbit antibodies to the chemically synthesized normal polypeptide (SEQ ID NO:1), Group B rats were treated with the same antibodies and the polypeptide itself. Group C is the control group. The error bars indicate ±1 standard deviation (S.D.).

The bone mineral apposition rate was determined by measurements, described above, of the lower right femoral metaphysis. The results are given in Table Five and FIG. 5.

TABLE FIVE

Bone Mineral Apposition Rates in Rats Injected with Antibody to the Chemically Synthesized Peptide

|  | Group A | Group B | Group C |
|---|---|---|---|
| Mean (μm/day) | 0.86 | 1.22 | 1.30 |
| S.D. | 0.02 | 0.08 | 0.11 |
| N | 5 | 5 | 5 |

|  | t | d.f. | p |
|---|---|---|---|
| Group A vs B | 8.06 | 8 | >0.2 |
| Group A vs C | 7.57 | 8 | <0.001 |
| Group B vs C | 1.24 | 8 | >0.2 |

Methodology and products can be thus be developed using antibody to the polypeptide for use in detecting the polypeptide with which the antibody binds. For example, antibody can be linked to or conjugated with any of several well known reporter systems set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluorescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such a method based on antigenic response to the chemically synthesized human polypeptide (SEQ ID NO:1) could be developed and variants of the polypeptide obtained, as described above for amino acid substitution, deletion and addition, (and conjugates) could then be pre-screened as potential bone stimulating factors. Those that react positively with the antibody to the already known peptide could then be tested for bone stimulatory effects in vivo using the system described herein for rats, for example.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

Figure 6:
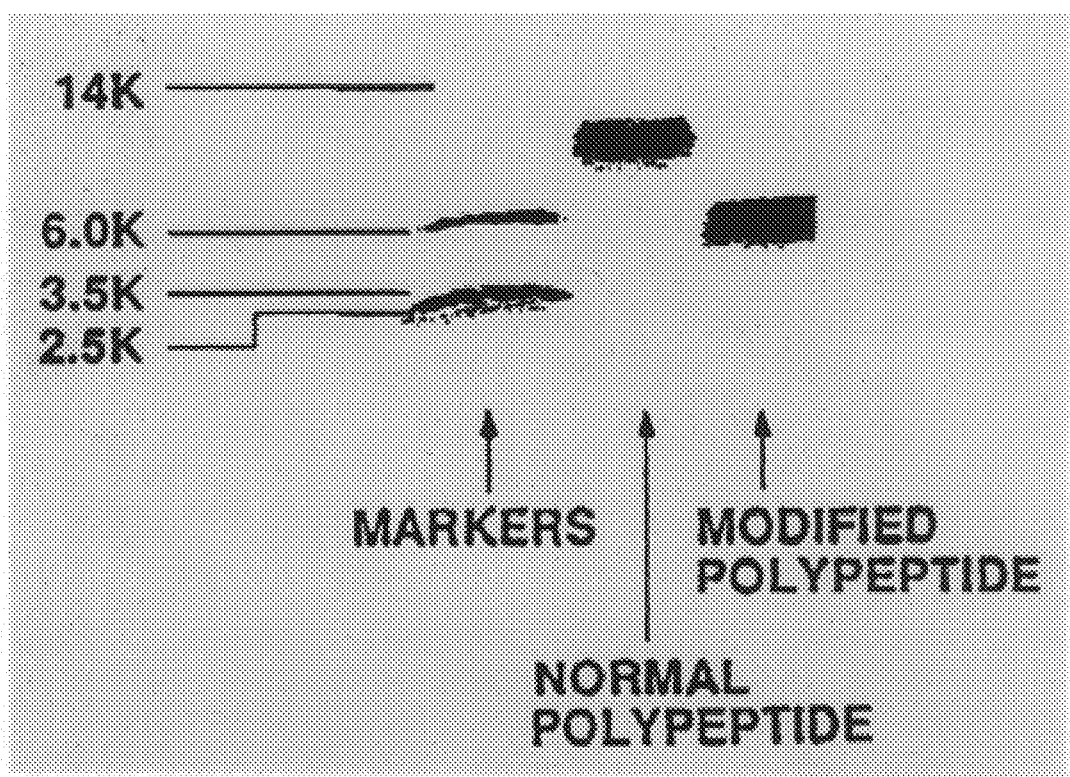
FIG. 6 shows a tricine SDS electrophoretic gel of the human chemically synthesized polypeptide (SEQ ID NO:1) and the same polypeptide containing a cys-ala substitution (SEQ ID NO:3).

Experiments Involving Chemically Synthesized Human Polypeptide Containing Cysteine-alanine Substitution A modified sequence (SEQ ID NO:3) of the chemically synthesized peptide (SEQ ID NO:1) obtained by substitution of the cysteine residue at position 13 by alanine was prepared by standard chemical procedures. An alanine residue is sterically similar to a reduced cysteine residue while rendering the polypeptide incapable of spontaneous dimerization. A tricine SDS electrophoretic gel of the modified and unmodified (normal) peptides is shown in FIG. 6.

Experiments were carried out on three groups of six rats weightin between 295 and 320 g. A 1 mg per ml solution of the modified peptide (SEQ ID NO:3) was prepared in 0.1% acetic acid. A 1 mg per ml solution of the normal peptide (SEQ ID NO:1) was prepared in 0.1% acetic acid. Each rat of a first of the groups had subcutaneously injected into its right thigh 0.1 ml of the modified peptide solution. Similarly, each rat of the second group was injected with 0.1 ml of the normal peptide solution. Each rat of the third group, the control group, was injected with 0.1 ml of 0.1% acetic acid solution. Immediately following these injections, each rat was injected intramuscularly with 24 mg per Kg body weight of tetracycline hydrochloride dissolved in 0.5 ml of water. A second dose of tetracycline hydrochloride was administered 48 hours later. The animals were sacrificed 24 hours after the second dose by $CO_2$ narcosis. The lower metaphysis of the right femur was dissected out and fixed in a 10% aqueous solution of formaldehyde buffered at pH 7.2 by acetate buffer. Bone sections were prepared for measurement as described above.

Figure 7:
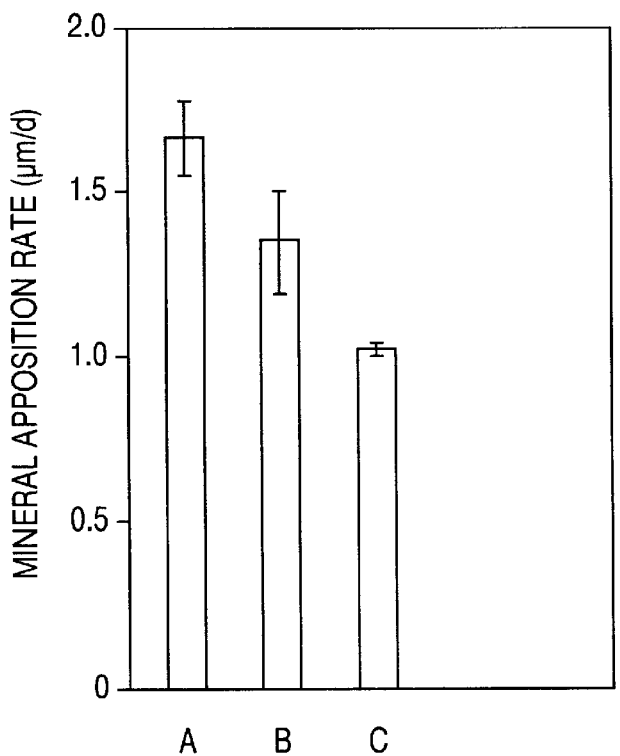
FIG. 7 graphically depicts the bone mineral apposition rate ($\mu$m per day) in rats injected with the chemically synthesized human polypeptide (SEQ ID NO:1), Group A; the modified chemically synthesized human polypeptide (SEQ ID NO:3). Group B; and control, Group C. (N=6 for all groups). The error bars indicate ±1 standard deviation (S.D.).

The results are tabulated in Table Six and graphically depicted in FIG. 7. As can be seen, the bone apposition rate for rats injected with the modified polypeptide is significantly greater than that for those of the control group but below the bone apposition rate shown for the rats injected with the normal peptide.

TABLE SIX

Comparison of the Group Arithmetic Means Among Groups Injected with Modified Peptide, Unmodified Peptide and Control

|  | Group A | Group B | Control Group |
|---|---|---|---|
| Mean (μm/day) | 1.67 μm/d | 1.35 μm/d | 1.02 μm/d |
| S.D. | 0.11 μm/d | 0.16 μm/d | 0.010 μm/d |
| N | 6 | 6 | 6 |

|  | t | d.f | p |
|---|---|---|---|
| Group A vs Control (Group C) | 12.2 | 10 | <0.001 |
| Group B vs Control (Group C) | 4.69 | 10 | <0.001 |
| Group A vs Group B | 3.97 | 10 | <0.005 |

Experiments Involving Active Fragments of the 36-Amino Acid Human Polypeptide

Polypeptides having the amino acid sequences identified as SEQ ID NOs:4, 5, 6, 7, 8 and 9 were synthesized according to well known chemical procedures.

Sprague-Dawley rats were used as test animals to determine bone mineral apposition rate, as described above. Male rats having weights between 280 and 380 g were subject to subcutaneous injection after one week of acclimatization. Each animal was injected with 200 μl of a 0.1% acetic acid test solution, solutions having been prepared at concentrations to obtain a dosage of about 25 nmol of polypeptide per animal. Each test dose was immediately followed by intramuscular injection of 24 mg per Kg of body weight of tetracycline hydrochloride. A second injection of tetracycline was made 48 hours later.

Control Group: 0.1% Acetic Acid Solution
Group A: SEQ ID NO:1:
  Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro
Group E: SEQ ID NO:4:
  Gly Ile Gly Lys Arg Thr Asn Glu His Thr Ala Asp Cys Lys Ile Lys Pro Asn Thr Leu His Lys Lys Ala Ala Glu Thr Leu Met Val
Group D: SEQ ID NO:5:
  Gly Ile Gly Lys Arg Thr Asn Glu His Thr Ala Asp Cys Lys Ile Lys Pro Asn Thr Leu His Lys Lys Ala Ala
Group C: SEQ ID NO:6:
  Gly Ile Gly Lys Arg Thr Asn Glu His Thr Ala Asp Cys Lys Ile Lys Pro Asn Thr Leu
Group B: SEQ ID NO:7:
  Gly Ile Gly Lys Arg Thr Asn Glu His Thr Ala Asp Cys Lys Ile In a similar but separate set of experiments, bone mineral apposition rates were tested using the following chemically synthesized polypeptides.

Figure 8:
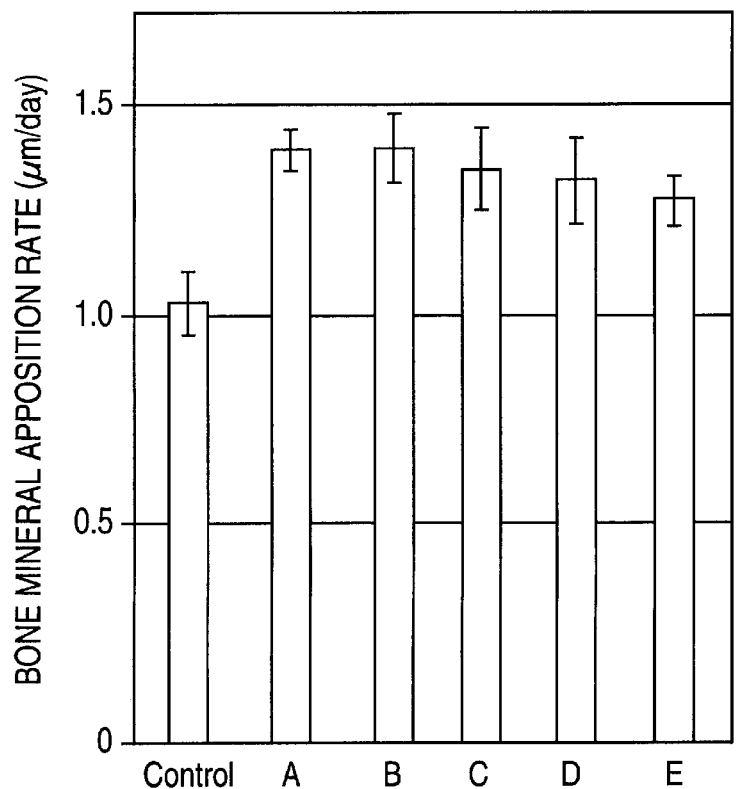
FIG. 8 graphically depicts the bone mineral apposition rate (μm per day) in rats injected with N-terminus chemically synthesized polypeptides: SEQ ID NO:1 (Group A); SEQ ID NO:7 (Group B); SEQ ID NO:6 (Group C); SEQ ID NO:5 (Group D); and SEQ ID NO:4 (Group E). (N=6 for all groups). The error bars indicate ±1 standard deviation (S.D.).
Figure 9:
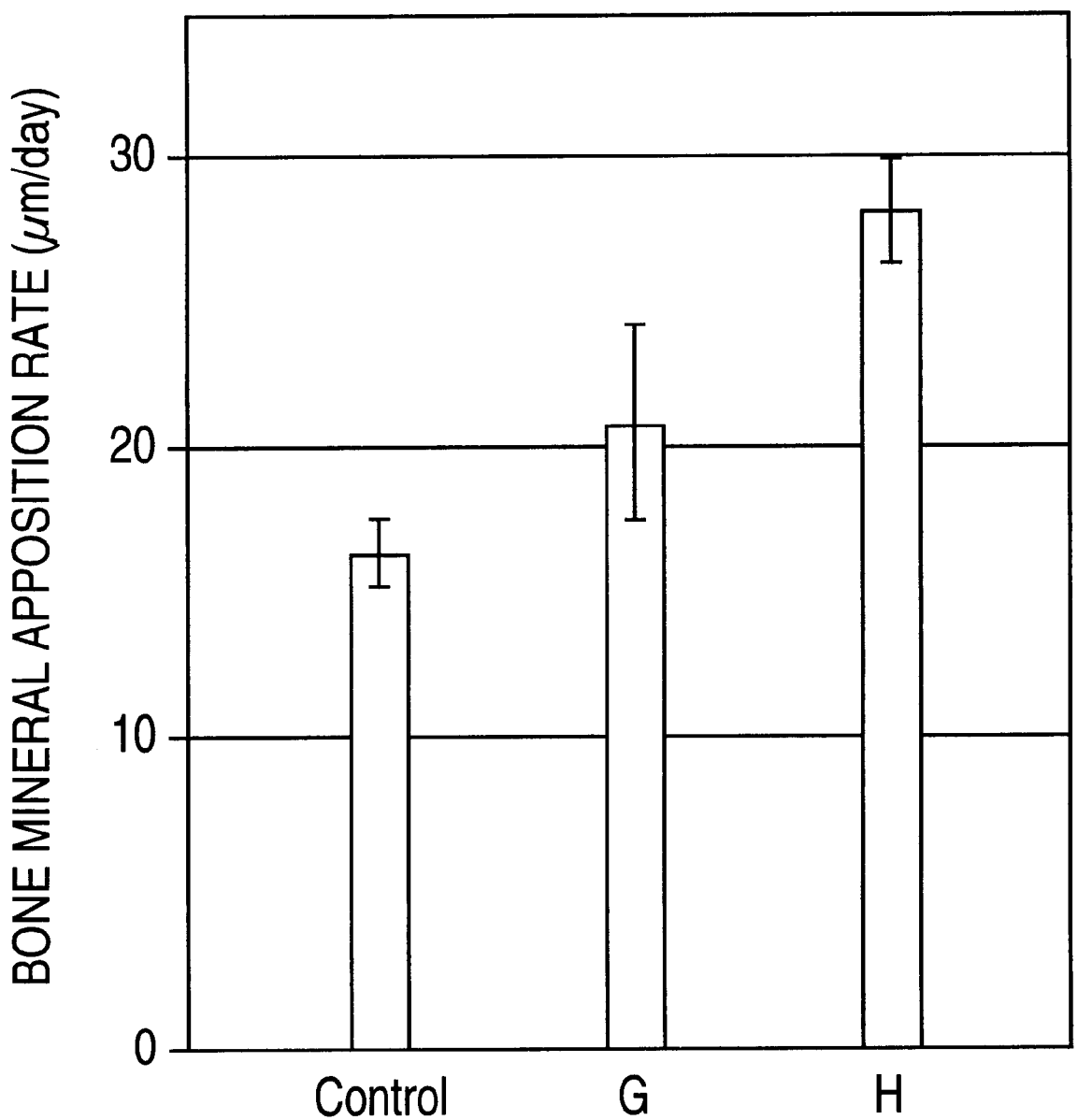
FIG. 9 graphically depicts the bone mineral apposition rate (μm per day) in rats injection with chemically synthesized polypeptides: SEQ ID NO:8 (Group G); SEQ ID NO:9 (Group H).

Group F: SEQ ID NO:8:
  Gly Ile Gly Lys Arg Thr Asn Glu His Thr Ala Asp Cys Lys
Group G: SEQ ID NO:9:
  Arg Thr Asn Glu His Thr Ala Asp Cys Lys Bone mineral apposition rates were determined by measurements of the lower metaphysis of the right femur, as described previously. Results obtained in the two sets of experiments are summarized in Tables Seven and Eight and graphically depicted in FIGS. 8 and 9. As can be seen, all of the polypeptides tested had a positive effect on bone apposition rate, i.e., displayed bone stimulatory activity.

TABLE SEVEN

Comparison of the Group Arithmetic Means Among First Groups Injected with Active Variants

|  | Group A | Group B | Group C | Group D | Group E | Control |
|---|---|---|---|---|---|---|
| Mean | 1.40 | 1.41 | 1.37 | 1.35 | 1.31 | 1.03 |
| S.D. | 0.05 | 0.08 | 0.09 | 0.10 | 0.06 | 0.06 |
| N | 6 | 6 | 6 | 6 | 6 | 6 |

|  | t | d.f. | p |
|---|---|---|---|
| Group A vs Control | 5.18 | 10 | <0.001 |
| Group B vs Control | 9.67 | 10 | <0.001 |
| Group C vs Control | 7.64 | 10 | <0.001 |
| Group D vs Control | 6.92 | 10 | <0.001 |
| Group E vs Control | 7.99 | 10 | <0.001 |
| Group A vs Group B | 0.14 | 10 | >0.5 |
| Group A vs Group C | 0.40 | 10 | >0.5 |
| Group A vs Group D | 0.66 | 10 | >0.5 |
| Group A vs Group E | 1.30 | 10 | >0.2 |
| Group B vs Group C | 0.82 | 10 | >0.4 |
| Group B vs Group D | 1.19 | 10 | >0.2 |
| Group B vs Group E | 2.49 | 10 | <0.05 |

TABLE EIGHT

Comparison of the Group Arithmetic Means Among Second Groups Injected with Active Variants

|  | Group F | Group G | Control Group |
|---|---|---|---|
| Mean (μm/day) | 2.09 μm/d | 2.83 μm/d | 1.63 μm/d |
| S.D. | 0.34 μm/d | 0.19 μm/d | 0.13 μm/d |
| N | 4 | 3 | 4 |

|  | t | d.f | p |
|---|---|---|---|
| Group F vs Control | 6 | 0.0470 |
| Group G vs Control | 5 | 0.0002 |
| Group F vs Group G | 5 | 0.215 |

Bone Calcium Content Experiments Involving SEQ ID NO:7

A further set of experiments was conducted using the polypeptide identified as SEQ ID NO:7 to determine the effect of the polypeptide on bone calcium content when administered to rats.

Ovariectomies were performed on rats as described above. A 0.1% acetic acid solution containing 25 nmoles of the polypeptide was administered subcutaneously to each rat each day for the duration of the experiment. One group of rats was treated for 12 weeks beginning 100 days after ovariectomization. Another group of rats was treated for eight weeks beginning eight weeks after ovariectomization. Rats were sacrificed at the end of the treatment period and dissected and post mortem assessment of bone and mineral content was carried out.

Figure 10:
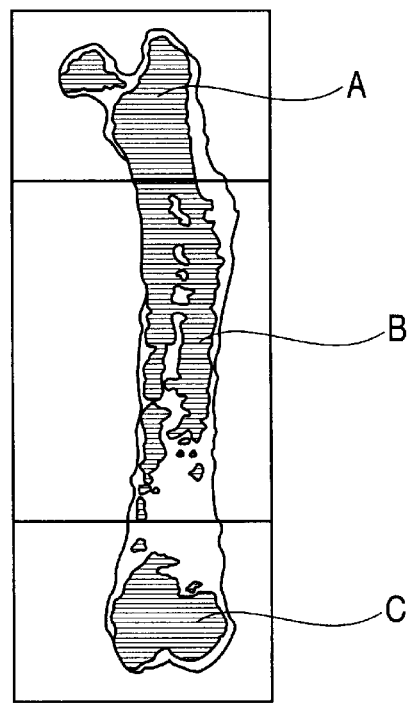
FIG. 10 is a DEXA image of a right femur of a rat showing scanned areas: A, proximal end; B, diaphysis; and C, distal end.
Figure 11:
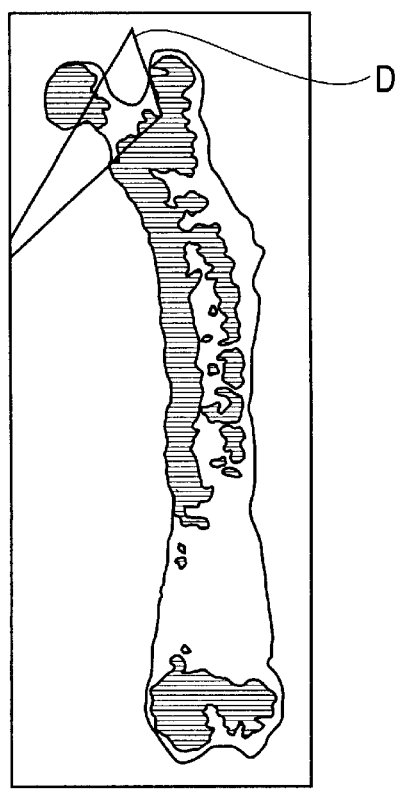
FIG. 11 is a DEXA image of a right femur of a rat showing scanned neck area.

The lumbar spines L1–L4 were cleaned with a power nylon brush to remove the attached muscle. They were placed ventral side down under 3 cm of distilled water in a polypropylene container and scanned by a dual energy x-ray absorptometer (DEXA), Hologic 100, to determine the calcium content in grams. The right femur of each rat was also dissected out intact and cleared of the attached muscles with a power nylon brush. It was scanned dorsal side down under 3 cm of distilled water by DEXA. Four regions of the femur were scanned, as indicated in FIGS. 10 and 11: A, proximal end; B, diaphysis; C, distal end; and D, neck. The bone mineral (i.e., calcium) content in grams was estimated in the four zones of the femur based on absorption and using an internal standard of the machine.

Results are tabulated in Tables Nine to Eighteen.

TABLE NINE

Comparison of Group Arithmetic Means Among Groups Injected with Polypeptide SEQ ID NO: 7 Administered over 100 Days to Ovariectomized Rats - Bone Mineral Content Measured in Proximal End of Femur

|  | Control | A-Ovariectomized (no polypeptide) | B-Ovariectomized (with polypeptide) |
|---|---|---|---|
| Mean (g.) | 0.1503 | 0.1351 | 0.1411 |
| S.D. | 0.0159 | 0.0105 | 0.0155 |
| N | 14 | 14 | 11 |

|  | t | d.f | p |
|---|---|---|---|
| Control vs A | 2.9772 | 26 | <0.025 |
| Control vs B | 1.4400 | 23 | N.S. |
| Group A vs Group B | 1.1634 | 23 | N.S. |

TABLE TEN

Comparison of Group Arithmetic Means Among Groups Injected with Polypeptide SEQ ID NO: 7 Administered over 56 Days to Ovariectomized Rats - Bone Mineral Content Measured in Proximal End of Femur

|  | Control | Sham | A-Ovariectomized (no polypeptide) | B-Ovariectomized (no polypeptide) |
|---|---|---|---|---|
| Mean (g.) | 0.1451 | 0.1387 | 0.1368 | 0.1328 |
| S.D. | 0.0183 | 0.0166 | 0.0280 | 0.0141 |
| N | 5 | 5 | 6 | 6 |

|  | t | d.f | p |
|---|---|---|---|
| Control vs Sham | 0.7372 | 8 | N.S. |
| Control vs A | 0.6261 | 9 | N.S. |
| Control vs B | 1.6223 | 9 | N.S. |
| Sham vs A | 0.1330 | 9 | N.S. |
| Sham vs B | 1.6229 | 9 | N.S. |
| Group A vs B | 0.3116 | 10 | N.S. |

TABLE ELEVEN

Comparison of Group Arithmetic Means Among Groups Injected with Polypeptide SEQ ID NO: 7 Administered over 100 Days to Ovariectomized Rats - Bone Mineral Content Measured in Spine (L1–L4)

|  | Control | A-Ovariectomized (no polypeptide) | B-Ovariectomized (with polypeptide) |
|---|---|---|---|
| Mean (g.) | 0.5437 | 0.4364 | 0.4758 |
| S.D. | 0.0161 | 0.0089 | 0.0188 |
| N | 14 | 14 | 10 |

|  | t | d.f | p |
|---|---|---|---|
| Control vs A | 5.8384 | 26 | <0.001 |
| Control vs B | 2.7434 | 22 | <0.0025 |
| Group A vs Group B | 2.0756 | 22 | <0.005 |

TABLE TWELVE

Comparison of Group Arithmetic Means Among Groups Injected with Polypeptide SEQ ID NO: 7 Administered over 56 Days to Ovariectomized Rats - Bone Mineral Content Measured in Spine (L1–L4)

|  | Control | Sham | A-Ovariectomized (no polypeptide) | B-Ovariectomized (no polypeptide) |
|---|---|---|---|---|
| Mean (g.) | 0.5542 | 0.5321 | 0.4322 | 0.4606 |
| S.D. | 0.0275 | 0.0172 | 0.0226 | 0.0234 |
| N | 5 | 5 | 6 | 6 |

|  | t | d.f | p |
|---|---|---|---|
| Control vs Sham | 0.6805 | 8 | N.S. |
| Control vs A | 4.4196 | 9 | <0.005 |
| Control vs B | 3.1042 | 9 | <0.025 |
| Sham vs A | 2.8382 | 9 | <0.025 |
| Sham vs B | 1.9951 | 9 | N.S. |
| Group A vs Group B | 0.8759 | 10 | N.S. |

TABLE THIRTEEN

Comparison of Group Arithmetic Means Among Groups Injected with Polypeptide SEQ ID NO: 7 Administered over 100 Days to Ovariectomized Rats - Bone Mineral Content Measured in Femoral Diaphysis

|  | Control | A-Ovariectomized (no polypeptide) | B-Ovariectomized (no polypeptide) |
|---|---|---|---|
| Mean (g.) | 0.2258 | 0.2146 | 0.2347 |
| S.D. | 0.0261 | 0.0106 | 0.0215 |
| N | 14 | 14 | 11 |

|  | t | d.f | p |
|---|---|---|---|
| Control vs A | 0.8301 | 26 | N.S. |
| Control vs B | 0.9078 | 23 | N.S. |
| Group A vs Group B | 2.3079 | 23 | <0.05 |

TABLE FOURTEEN

Comparison of Group Arithmetic Means Among Groups Injected with Polypeptide SEQ ID NO: 7 Administered over 56 Days to Ovariectomized Rats - Bone Mineral Content Measured in Femoral Diaphysis

|  | Control | Sham | A-Ovariectomized (no polypeptide) | B-Ovariectomized (no polypeptide) |
|---|---|---|---|---|
| Mean (g.) | 0.2179 | 0.1918 | 0.1716 | 0.2091 |
| S.D. | 0.0156 | 0.0162 | 0.0272 | 0.0121 |
| N | 5 | 5 | 6 | 6 |

|  | t | d.f | p |
|---|---|---|---|
| Control vs Sham | 2.2590 | 8 | <0.05 |
| Control vs A | 3.3549 | 9 | <0.025 |
| Control vs B | 1.9209 | 9 | N.S. |
| Sham vs A | 1.4571 | 9 | N.S. |

TABLE FOURTEEN-continued

| | | | |
|---|---|---|---|
| Sham vs B | 1.1778 | 9 | N.S. |
| Group A vs Group B | 2.4926 | 10 | <0.05 |

TABLE FIFTEEN

Comparison of Group Arithmetic Means Among Groups Injected with Polypeptide SEQ ID NO: 7 Administered over 100 Days to Ovariectomized Rats - Bone Mineral Content Measured in Distal End of Femur

| | Control | A-Ovariectomized (no polypeptide) | B-Ovariectomized (no polypeptide) |
|---|---|---|---|
| Mean (g.) | 0.1597 | 0.1396 | 0.1424 |
| S.D. | 0.0185 | 0.0068 | 0.0132 |
| N | 14 | 14 | 11 |

| | t | d.f | p |
|---|---|---|---|
| Control vs A | 3.8255 | 26 | <0.001 |
| Control vs B | 2.6160 | 23 | <0.025 |
| Group A vs Group B | 0.6984 | 23 | N.S. |

TABLE SIXTEEN

Comparison of Group Arithmetic Means Among Groups Injected with Polypeptide SEQ ID NO: 7 Administered over 56 Days to Ovariectomized Rats - Bone Mineral Content Measured in Distal End of Femur

| | Control | Sham | A-Ovariectomized (no polypeptide) | B-Ovariectomized (no polypeptide) |
|---|---|---|---|---|
| Mean (g.) | 0.1826 | 0.1540 | 0.1304 | 0.1347 |
| S.D. | 0.0122 | 0.0118 | 0.0094 | 0.0039 |
| N | 5 | 5 | 6 | 6 |

| | t | d.f | p |
|---|---|---|---|
| Control vs Sham | 3.7549 | 8 | <0.025 |
| Control vs A | 8.0183 | 9 | <0.001 |
| Control vs B | 9.1462 | 9 | <0.001 |
| Sham vs A | 3.7046 | 9 | <0.005 |
| Sham vs B | 3.8149 | 9 | <0.005 |
| Group A vs B | 1.0274 | 10 | N.S. |

TABLE SEVENTEEN

Comparison of Group Arithmetic Means Among Groups Injected with Polypeptide SEQ ID NO: 7 Administered over 100 Days to Ovariectomized Rats - Bone Mineral Content Measured in Femoral Neck

| | Control | A-Ovariectomized (no polypeptide) | B-Ovariectomized (no polypeptide) |
|---|---|---|---|
| Mean (g.) | 0.0334 | 0.0303 | 0.0351 |
| S.D. | 0.0049 | 0.0040 | 0.0031 |
| N | 14 | 14 | 10 |

| | t | d.f | p |
|---|---|---|---|
| Control vs A | 1.3978 | 26 | N.S. |
| Control vs B | 1.0326 | 21 | N.S. |
| Group A vs B | 2.2590 | 21 | P < 0.005 |

TABLE EIGHTEEN

Comparison of Group Arithmetic Means Among Groups injected with Polypeptide SEQ ID NO:7 Administered over 56 Days to Ovariectomized Rats-Bone Mineral Content Measured in Femoral Neck

| | Control | Sham | A-Ovariectomized (no polypeptide) | B-Ovariectomized (with polypeptide) |
|---|---|---|---|---|
| Mean (g.) | 0.0277 | 0.0265 | 0.0202 | 0.0274 |
| S.D. | 0.0020 | 0.0038 | 0.0028 | 0.0013 |
| N | 5 | 5 | 6 | 6 |

| | t | d.f | p |
|---|---|---|---|
| Control vs Sham | 1.1534 | 8 | N.S. |
| Control vs A | 4.9809 | 9 | <0.001 |
| Control vs B | 0.3342 | 9 | N.S. |
| Sham vs A | 2.6620 | 9 | <0.05 |
| Sham vs B | 1.1462 | 9 | N.S. |
| Group A vs B | 5.6713 | 10 | <0.005 |

As can be seen from the tabulated data, the increase in in vivo calcium bone content is most obvious in the femoral neck and femoral diaphysis, implying that the effect of the administered peptide can be site specific, possibly being greater at skeletal sites under mechanical stress.

Experiments Involving Other Fragments of the 36-Amino Acid Human Polypeptide

Polypeptide fragments of the normal polypeptide (SEQ ID NO:1) were also synthesized and tested for bone stimulatory activity as with the C-terminus fragments.

Control Group: 0.1% Acetic Acid

Group H: SEQ ID NO:1:

Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro

Group I: SEQ ID NO:16:

Arg Thr Asn Glu His Thr Ala Asp Cys Lys Ile

Group J: SEQ ID NO:15:

Arg Thr Asn Glu His Thr Ala Asp Cys Lys Ile Lys Pro Asn Thr Leu His Lys Lys Ala Ala Glu Thr Leu Met Val Leu Asp Gln Asn

Group K: SEQ ID NO:14:

Thr Ala Asp Cys Lys Ile Lys Pro Asn Thr Leu His Lys Lys Ala Ala Glu Thr Leu Met Val Leu Asp

Group L: SEQ ID NOs:10,11,12 & 13 (mixture):

Leu His Lys Lys Ala Ala Glu Thr Leu Met Val Leu Asp Gln Asn Gln Leu His Lys Lys Ala Ala Glu Thr Leu Met Val Leu Asp Gln Asn Leu His Lys Lys Ala Ala Glu Thr Leu Met Val Leu Asp Gln Leu His Lys Lys Ala Ala Glu Thr Leu Met Val Leu Asp

Figure 12:
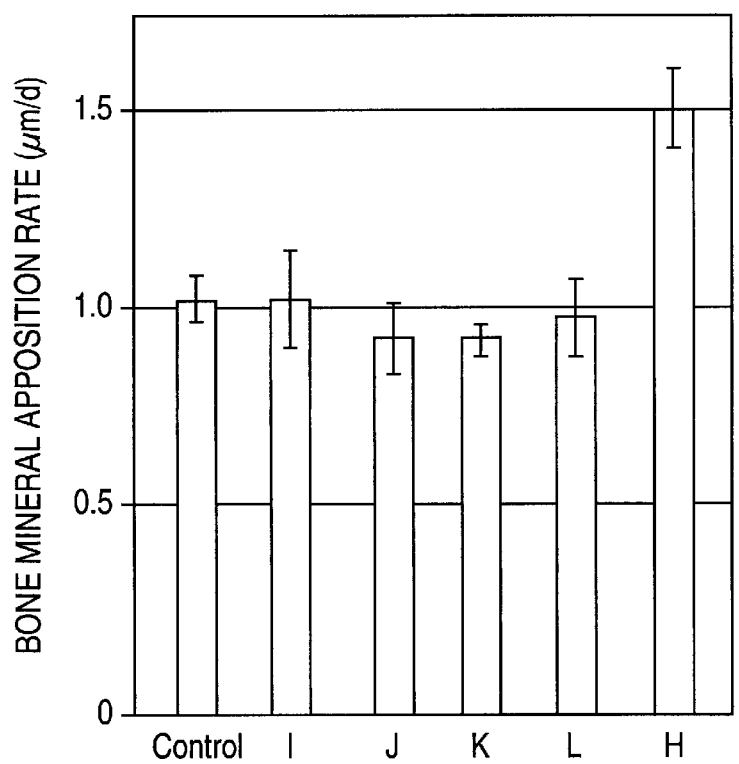
FIG. 12 graphically depicts the bone mineral apposition rate (μm per day) in rats injected with non-N-terminus chemically synthesized polypeptide fragments SEQ ID NO:1 (Group H); SEQ ID NO:16 (Group I); SEQ ID NO:15 (Group J); SEQ ID NO:14 (Group K); and SEQ ID NOs:10, 11,12 & 13 (Group L). (N=6 for all groups). The error bars indicate ±1 standard deviation (S.D.).

Bone mineral apposition rates were again determined by measurement of the lower metaphysis of the right femur. Results obtained are summarized in Table Nineteen and graphically depicted in FIG. 12. As can be seen in FIG. 12, none of the non-N-terminus variants identified as SEQ ID NO:10, 11, 12, 13, 14, 15 or 16 was found to increase the bone apposition rate with respect to the control.

TABLE NINETEEN

Summary of the Group Arithmetic Means for Bone Apposition Rates of Rats injected with Non-N-terminus Variants

|  | Group H | Group I | Group J | Group K | Group L | Control |
|---|---|---|---|---|---|---|
| Mean (μm/day) | 1.50 | 1.02 | 0.92 | 0.92 | 0.98 | 1.02 |
| S.D. | 0.09 | 0.12 | 0.09 | 0.04 | 0.09 | 0.06 |
| N | 6 | 6 | 6 | 6 | 6 | 6 |

A summary of the results obtained with respect to particular polypeptide sequences tested is provided in FIG. 13.

As can be seen, the polypeptide identified as SEQ ID NO:9 has a sequence of 10 amino acids contained in the 36 amino acid sequence of the polypeptide identified as SEQ ID NO:1, i.e., in vivo bone stimulatory activity can be retained with a polypeptide in which as little as 28% of the amino acid sequence of SEQ ID NO:1 is conserved. Bone stimulatory effects would also be expected to be observed for homologues of the polypeptide identified as SEQ ID NO:9. It may even be found that one or more of the amino acids present in SEQ ID NO:9 could be deleted and activity of the polypeptide (or homologue) be retained.

Of course it is known to those skilled in the art that polypeptides which provide similar activity are generally related by having the same or similar three-dimensional portion(s) which interacts with another agent, such as a receptor with which the polypeptide binds in some way. This is why it is possible to have several polypeptides that are related to each other that display similar bone-stimulating activity.

The present invention provides a synthetic polypeptide having in vivo bone stimulatory activity in mammals and which increases calcium density or content in bones of mammals, having an amino acid sequence which is at least about 19% conserved in relation to the amino acid sequence identified as SEQ ID NO:1 and having at least one amino acid deleted therefrom, or a homologue thereof. In the context of this invention, a peptide containing an amino acid sequence that can be aligned with that of SEQ ID NO:1 such that at least about 30% of individual amino acid residues of the original sequence are present in the peptide is said to be about 30% conserved with the amino acid sequence identified as SEQ ID NO:1, allowing for homologous substitutions and a limited number of insertions or deletions between aligned sequences. An amino acid sequence having seven out of the 36 amino acid residues of SEQ ID NO:1 in aligned sequence would be 19% conserved. An amino acid sequence having eight out of the 36 amino acid residues of SEQ ID NO:1 in aligned sequence would be 22% conserved. An amino acid sequence having nine out of the 36 amino acid residues of SEQ ID NO:1 in aligned sequence would be 25% conserved. An amino acid sequence having ten out of the 36 amino acid residues of SEQ ID NO:1 in aligned sequence would be 28% conserved.

Described in a slightly different way, a polypeptide of the present invention is an amino acid sequence corresponding to SEQ ID NO:1 with (a) one amino acid to 4 amino acids deleted from the N-terminus of SEQ ID NO:1, (b) one to 22 amino acids deleted from the C-terminus of SEQ ID NO:1, or both (a) and (b); or a functionally equivalent homologue. It may be found possible to delete 5 or 6 more amino acids from the N-terminus or to delete more than 22 amino acids from the C-terminus of SEQ ID NO:1.

In another sense, the polypeptide of the present invention can be described as a polypeptide exhibiting bone stimulatory activity in mammals, the polypeptide having the sequence identified as SEQ ID NO:1, SEQ ID NO:3, SEQ ID NO:4, SEQ ID NO:5, SEQ ID NO:4, SEQ ID NO:6, SEQ ID NO:7, SEQ ID NO:8, or SEQ ID NO:9; analogues thereof wherein the amino acids in the sequence may be substituted, deleted or added, so long as the bone stimulatory activity in mammals derived from the three dimensional structure of the sequence is preserved; and conjugates of each of the polypeptides or analogues thereof, wherein if the polypeptide sequence has that identified as SEQ ID NO:1, then there is at least one amino acid deleted therefrom.

A polypeptide of the present invention would include such a sequence which sequence would have a molecular weight in the range of from about 1000 to 4000. It is to be understood however that the sequence might be added to by conjugation or other technique, which could increase the molecular weight of the overall compound beyond 4000.

It will also be understood, without the intention of being limited thereby, that a variety of substitutions of amino acids is possible while "preserving" the threee-dimensional structure responsible for the bone stimulatory effect of the polypeptides disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. This being said, the linkage of the peptides together by the disulfide bridge appears to be of some importance, and so the lone cysteine residue should probably be held intact and other amino acids capable of forming a disulfide linkage should not be substituted elsewhere in the sequence, although as seen above a successful cys-ala substitution was effected (SEQ ID NO:3). Substitutions among the charged acidic amino acids, aspartic acid and glutamic acid, could probably be made, as could substitutions among the charged basic amino acids, lysine and arginine. Substitutions among the aromatic amino acids, icluding phenylalanine, histidine, tryptophan and tyrosine would also likely be possible. Substitutions can be made alone or in combination. These sorts of substitutions and interchanges are well known to those skilled in the art. U.S. Pat. Nos. 5,487,983 and 5,512,548, for instance, describes other possible substitutions including substitutions involving amino acids not encoded by the gene. Other substitutions might well be possible.

The importance of the N-terminus portion of the sequence is evident from the results described herein. The polypeptide (SEQ ID NO:9) having amino acids 5 to 14 of SEQ ID NO:1 displays bone stimulatory activity while polypeptides lacking the first nine N-terminus amino acids, but having amino acids 10 to 32 (SEQ ID NO:14) or amino acids 20 to 35 (SEQ ID NO:10) do not display bone stimulatory activity. It may be that it is possible to delete more amino acids from either end of the polypeptide identified as SEQ ID NO:9 while retaining the three-dimensional configuration of the subsequence of the polypeptide responsible for bone stimulatory activity. Internal deletions, although they might be possible to some limited extent, should be few. Of particular note, is the polypeptide having the sequence identified as SEQ ID NO:16, which differs by only one amino acid residue from the amino acid sequence identified as SEQ ID NO:9. The former does not display activity while the latter does display bone stimulatory activity. It is possible using the experimental methods disclosed herein to distinguish between sequences which do and do not stimulate bone growth and which do and do not increase calcium bone content.

It should still be possible for minor additions of amino acids to be made at the ends of the sequence and symmetrical or nearly symmetrical additions to the carboxy and amino terminals are likely to be possible. Internal additions, although likely to be possible to some limited extent, should be few.

Of the above-lised modifications to the sequence, terminal additions, deletions or substitutions are most likely to be most useful, as such a modification can serve a variety of functions: an identifying group as for use in a radioimmunoassay; or a linking group, as examples.

As with the normal peptide (SEQ ID NO:1), an active subsequence containing a cysteine residue (i.e., SEQ ID NOs:4, 5, 6, 7, 8 or 9) is likely to spontaneously dimerize and exist in the dimeric form.

A further advantage may be obtained through chimeric forms of the protein, as known in the art. A DNA sequence encoding the entire protein, or a portion of the protein, could thus be linked with a sequence coding for the C-terminal portion of *E. coli* β-galactosidase to produce a fusion protein, for example. An expression system for human respiratory syncytial virus glycoproteins F and G is described in U.S. Pat. No. 5,288,630, issued Feb. 22, 1994, and references cited therein, for example.

A polypeptide of the present invention would usually be synthetic, whether prepared by techniques of conventional "chemistry" or by recombinant techniques. Here, a polypeptide so produced is referred to as being substantially pure or biochemically pure when it is generally free of polypeptides or proteins with which it would occur if found directly in nature, as in blood serum from an animal, for example.

The references, patents, and patent applications cited herein are incorporated by reference in their entireties to the same extent as if they were individually incorporated by reference.

Nucleic acid (DNA) sequences coding for the active portions of the normal polypeptide would be as follows:

SEQ ID NO:17 (corresponding to SEQ ID NO:4):

GGG ATC GGA AAA CGA ACA AAT GAA CAT ACG GCA GAT TGT AAA ATT AAA CCG AAC ACC TTG CAT AAA AAA GCT GCA GAG ACT TTA ATG GTC

SEQ ID NO:18 (corresponding to SEQ ID NO:5):

GGG ATC GGA AAA CGA ACA AAT GAA CAT ACG GCA GAT TGT AAA ATT AAA CCG AAC ACC TTG CAT AAA AAA GCT GCA

SEQ ID NO:19 (corresponding to SEQ ID NO:6):

GGG ATC GGA AAA CGA ACA AAT GAA CAT ACG GCA GAT TGT AAA ATT AAA CCG AAC ACC TTG

SEQ ID NO:20 (corresponding to SEQ ID NO:7):

GGG ATC GGA AAA CGA ACA AAT GAA CAT ACG GCA GAT TGT AAA ATT

SEQ ID NO:21 (corresponding to SEQ ID NO:8):

GGG ATC GGA AAA CGA ACA AAT GAA CAT ACG GCA GAT TGT AAA

SEQ ID NO:22 (corresponding to SEQ ID NO:9):

CGA ACA AAT GAA CAT ACG GCA GAT TGT AAA

Accordingly, a vector incorporating such a DNA sequence could be constructed for use in synthesizing a polypeptide, as described previously, and particularly in international patent application No. PCT/CA 94/00144. The DNA sequence coding for the polypeptide identified as SEQ ID NO:1 is given as SEQ ID NO:23 in the sequence listing of this specification.

A DNA sequence or fragment of the present invention may be any fragment that contains a nucleotide sequence which encodes a polypeptide of the present invention. In addition to any of the above coding sequences, the DNA fragment can have an appropriate promoter and an SD sequence (or a suitable ribosome binding site) at its 5'-end, and if necessary, a nucleotide sequence containing a translation initiation codon at the 5'-end and a nucleotide sequence containing a termination codon at the 3'-end.

As known to those skilled in the art, the genetic code is "degenerate". A nucleotide in a gene sequence can thus be replaced by another nucleotide in accordance with the degeneracy of a particular codon (coding triplet), without changing the amino acid sequence of the polypeptide coded for by the gene. A DNA fragment of the present invention can thus be derived from any of the above sequences (and DNA sequences corresponding to substituted polypeptide or other analogues not explicitly illustrated), and such replacement might be done in such a way that the resulting codon(s) shows a high utilization frequency in a specific host cell when producing a polypeptide of the present invention using genetic engineering techniques.

It will of course be understood, that anitbodies to any of the polypeptides disclosed herein could be generated, as described in connection with the normal polypeptide (SEQ ID NO:1).

A polypeptide of the present invention can be made into a pharmaceutical preparation suitable for use in efficient administration to a patient in need of such administration, as person suffering from a reduction in bone formation, for example. Prophylactic treatment is another possibility. Injection appears to be a likely candidate as a route of administration. A pharmaceutical preparation would include a proper carrier or medium such as sterile water, physiological saline, a plant oil, a non-toxic organic solvent or the like generally used in drug preparations. A filler, colouring agent, emulsifying agent, suspending agent, stabilizer, a preservative or the like, etc. could also be used. Other possible administration routes include rectal, topical parenteral, ocular, nasal, sublingual, buccal, intravenous, etc. The form of a pharmaceutical could be a dispersion, solution, suspension, tablet, troche, etc. and could be in a slow or time release form or device.

The dosage would likely vary with the type of patient, age, sex, etc. and the nature and severity of the condition being treated. In general, dose range for treatment of a condition related to reduced bone formation would be in the range of from about .001 pmol to 100 nmol per kg of body weight of a patient.

What is claimed is:

1. An isolated polypeptide having bone stimulatory activity and comprising an amino acid sequence which includes up to 30 consecutive amino acids from the amino acid sequence identified as SEQ ID NO:4, provided that amino acids 5 to 14 of SEQ ID NO:4 are not deleted or a conservatively substituted variant thereof having bone stimulatory activity.

2. A conservatively substituted variant of a polypeptide according to claim 1.

3. A chimeric bone stimulating factor comprising a polypeptide of claim 1.

4. An agent for use in prevention and treatment of a bone reduction related disease which comprises a polypeptide of claim 1 as an active ingredient.

5. A pharmaceutical composition for promoting bone growth, comprising a therapeutically effective amount of a polypeptide of claim 1 in combination with a carrier.

6. A method of increasing bone growth in a mammal by administering a bone-growth-increasing effective amount of a polypeptide having an amino acid sequence of a polypeptide defined in claim 1.

7. A method of treating osteoporosis by administering to a mammal an amount effective for treating osteoporosis of a polypeptide of claim 1.

8. A method of promoting bone growth in a mammal by administering to a mammal a bone-growth-promoting effective amount of a polypeptide of claim 1.

9. A method for preparing a medicament for promoting bone growth or treating osteoporosis, comprising incorporating a polypeptide having a sequence according to claim 1 into the medicament.

10. An isolated DNA fragment which encodes said polypeptide of claim 1 or a DNA fragment which differs therefrom due to the degeneracy of the genetic code.

11. A vector comprising a DNA sequence which encodes said polypeptide of claim 1.

12. A process for producing a polypeptide of claim 1, which comprises:

a) preparing a DNA fragment containing a nucleotide sequence which encodes said polypeptide;

b) incorporating said DNA fragment into an expression vector to obtain a recombinant DNA fragment which contains said DNA fragment and is capable of undergoing replication;

c) transforming a host cell with said recombinant DNA fragment to isolate a transformant which can express said polypeptide; and d) culturing said transformant to allow the transformant to produce said polypeptide and recovering said polypeptide from resulting cultured mixture.

13. An isolated first polypeptide which includes up to 30 consecutive amino acids sufficiently duplicative of a second polypeptide which includes up to 30 consecutive amino acids from the amino acid sequence identified as SEQ ID NO:4, provided that amino acids 5 to 14 of SEQ ID NO:4 are not deleted, such that the first polypeptide is encoded by a DNA that hybridizes in about 1×SSC at 68° C. with DNA encoding the second polypeptide and has bone stimulatory activity.

14. A conservatively substituted variant of a polypeptide according to claim 13.

15. A chimeric bone stimulating factor comprising a polypeptide of claim 13.

* * * * *

```
                    SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
```

(A) LENGTH: 36 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Gly Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

(2) INFORMATION FOR SEQ ID NO:2:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is N-acetyl glycine"

(xi) SEQUENCE DESCRIPTION: SEQ ID NO:2:

Xaa Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

(2) INFORMATION FOR SEQ ID NO:3:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Gly Ile Gly Lys Arg Thr Asn Glu His Thr Ala Asp Ala Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

(2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Gly Ile Gly Lys Arg Thr Asn Glu His Thr Ala Asp Cys Lys Ile Lys
1               5                  10                  15

Pro Asn Thr Leu His Lys Lys Ala Ala Glu Thr Leu Met Val
            20                  25                  30

(2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Gly Ile Gly Lys Arg Thr Asn Glu His Thr Ala Asp Cys Lys Ile Lys
1               5                  10                  15

Pro Asn Thr Leu His Lys Lys Ala Ala
            20                  25

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Gly Ile Gly Lys Arg Thr Asn Glu His Thr Ala Asp Cys Lys Ile Lys
1               5                  10                  15

Pro Asn Thr Leu
            20

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Gly Ile Gly Lys Arg Thr Asn Glu His Thr Ala Asp Cys Lys Ile
1               5                  10                  15

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Gly Ile Gly Lys Arg Thr Asn Glu His Thr Ala Asp Cys Lys
1               5                  10

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Arg Thr Asn Glu His Thr Ala Asp Cys Lys
1               5                   10
```

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Leu His Lys Lys Ala Ala Glu Thr Leu Met Val Leu Asp Gln Asn Gln
1               5                   10                  15
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Leu His Lys Lys Ala Ala Glu Thr Leu Met Val Leu Asp Gln Asn
1               5                   10                  15
```

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Leu His Lys Lys Ala Ala Glu Thr Leu Met Val Leu Asp Gln
1               5                   10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Leu His Lys Lys Ala Ala Glu Thr Leu Met Val Leu Asp
1               5                   10
```

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Thr Ala Asp Cys Lys Ile Lys Pro Asn Thr Leu His Lys Lys Ala Ala
1               5                   10                  15

Glu Thr Leu Met Val Leu Asp
            20
```

(2) INFORMATION FOR SEQ ID NO:15:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Arg Thr Asn Glu His Thr Ala Asp Cys Lys Ile Lys Pro Asn Thr Leu
1               5                   10                  15

His Lys Lys Ala Ala Glu Thr Leu Met Val Leu Asp Gln Asn
            20                  25                  30
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Arg Thr Asn Glu His Thr Ala Asp Cys Lys Ile
1               5                   10
```

(2) INFORMATION FOR SEQ ID NO:17:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..90

(xi) SEQUENCE DESCRIPTION: SEQ ID NO:17:

```
GGG ATC GGA AAA CGA ACA AAT GAA CAT ACG GCA GAT TGT AAA ATT AAA    48
Gly Ile Gly Lys Arg Thr Asn Glu His Thr Ala Asp Cys Lys Ile Lys
1               5                   10                  15

CCG AAC ACC TTG CAT AAA AAA GCT GCA GAG ACT TTA ATG GTC            90
Pro Asn Thr Leu His Lys Lys Ala Ala Glu Thr Leu Met Val
            20                  25                  30
```

(2) INFORMATION FOR SEQ ID NO:18:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..75

(xi) SEQUENCE DESCRIPTION: SEQ ID NO:18:

```
GGG ATC GGA AAA CGA ACA AAT GAA CAT ACG GCA GAT TGT AAA ATT AAA      48
Gly Ile Gly Lys Arg Thr Asn Glu His Thr Ala Asp Cys Lys Ile Lys
 1               5                  10                  15

CCG AAC ACC TTG CAT AAA AAA GCT GCA                                  75
Pro Asn Thr Leu His Lys Lys Ala Ala
             20                  25
```

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..60

(xi) SEQUENCE DESCRIPTION: SEQ ID NO:19:

```
GGG ATC GGA AAA CGA ACA AAT GAA CAT ACG GCA GAT TGT AAA ATT AAA      48
Gly Ile Gly Lys Arg Thr Asn Glu His Thr Ala Asp Cys Lys Ile Lys
 1               5                  10                  15

CCG AAC ACC TTG                                                      60
Pro Asn Thr Leu
             20
```

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..45

(xi) SEQUENCE DESCRIPTION: SEQ ID NO:20:

```
GGG ATC GGA AAA CGA ACA AAT GAA CAT ACG GCA GAT TGT AAA ATT          45
Gly Ile Gly Lys Arg Thr Asn Glu His Thr Ala Asp Cys Lys Ile
 1               5                  10                  15
```

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(ix) FEATURE:
             (A) NAME/KEY: CDS
             (B) LOCATION: 1..42

(xi) SEQUENCE DESCRIPTION: SEQ ID NO:21:

GGG ATC GGA AAA CGA ACA AAT GAA CAT ACG GCA GAT TGT AAA           42
Gly Ile Gly Lys Arg Thr Asn Glu His Thr Ala Asp Cys Lys
 1               5                  10

(2) INFORMATION FOR SEQ ID NO:22:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..30

(xi) SEQUENCE DESCRIPTION: SEQ ID NO:22:

CGA ACA AAT GAA CAT ACG GCA GAT TGT AAA                           30
Arg Thr Asn Glu His Thr Ala Asp Cys Lys
 1               5                  10

(2) INFORMATION FOR SEQ ID NO:23:

(i) SEQUENCE CHARACTERISTICS:
             (A) LENGTH: 108 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..108

(xi) SEQUENCE DESCRIPTION: SEQ ID NO:23:

GGG ATC GGA AAA CGA ACA AAT GAA CAT ACG GCA GAT TGT AAA ATT AAA   48
Gly Ile Gly Lys Arg Thr Asn Glu His Thr Ala Asp Cys Lys Ile Lys
 1               5                  10                  15

CCG AAC ACC TTG CAT AAA AAA GCT GCA GAG ACT TTA ATG GTC AAA ATT   96
Pro Asn Thr Leu His Lys Lys Ala Ala Glu Thr Leu Met Val Lys Ile
                 20                  25                  30

AAA CCG AAC ACC                                                  108
Lys Pro Asn Thr
         35

(2) INFORMATION FOR SEQ ID NO:24:

(i) SEQUENCE CHARACTERISTICS:
             (A) LENGTH: 36 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:24:

Gly Ile Gly Lys Arg Thr Asn Glu His Thr Ala Asp Cys Lys Ile Lys
 1               5                  10                  15

```
                        -continued

Pro Asn Thr Leu His Lys Lys Ala Ala Glu Thr Leu Met Val Lys Ile
            20                  25                  30

Lys Pro Asn Thr
            35
```